(12) United States Patent
Smith et al.

(10) Patent No.: US 7,598,075 B2
(45) Date of Patent: Oct. 6, 2009

(54) APPARATUS AND METHODS FOR PRODUCING AND USING HIGH-DENSITY CELLS AND PRODUCTS THEREFROM

(75) Inventors: Gale E. Smith, Darnestown, MD (US); John Knell, Rockville, MD (US); Andrei I. Voznesensky, West Hartford, CT (US)

(73) Assignee: Protein Sciences Corporation, Meriden, CT (US)

( * ) Notice: Subject to any disclaimer, the term of this patent is extended or adjusted under 35 U.S.C. 154(b) by 101 days.

(21) Appl. No.: 11/097,994

(22) Filed: Apr. 1, 2005

(65) Prior Publication Data
US 2006/0019385 A1    Jan. 26, 2006

(51) Int. Cl.
*C12M 1/12* (2006.01)
(52) U.S. Cl. ................................................. 435/297.2
(58) Field of Classification Search ............... 435/297.2
See application file for complete search history.

(56) References Cited

U.S. PATENT DOCUMENTS

| | | | | | |
|---|---|---|---|---|---|
| 5,002,890 | A | * | 3/1991 | Morrison | 435/297.3 |
| 5,605,835 | A | * | 2/1997 | Hu et al. | 435/297.2 |
| 5,888,807 | A | * | 3/1999 | Palsson et al. | 435/293.2 |
| 6,048,727 | A | * | 4/2000 | Kopf | 435/383 |

\* cited by examiner

*Primary Examiner*—Walter D Griffin
*Assistant Examiner*—Lydia Edwards
(74) *Attorney, Agent, or Firm*—Frommer Lawrence & Haug LLP; Thomas J. Kowalski; Heather DiPietrantonio

(57) ABSTRACT

Disclosed and claimed is apparatus and methods for the growth of cells to high density, products therefrom and uses thereof. Also disclosed and claimed is the use of this method for the growth to high-density insect cells, such as the *Spodoptera frugiperda* Sf900+ cell line (ATCC: CRL 12579). Further disclosed is the infection of Sf900+ cells at high cell density with wild type and recombinant baculoviruses to produce baculovirus and DNA or gene or expression products.

6 Claims, 11 Drawing Sheets

Bioreactor                                                            Media Reservoir Bioreactor Media Reservoir Figure 5. Growth of Insect Cells in a High-Density Dialysis Bioreactor with In-Line Oxygen Sparging.
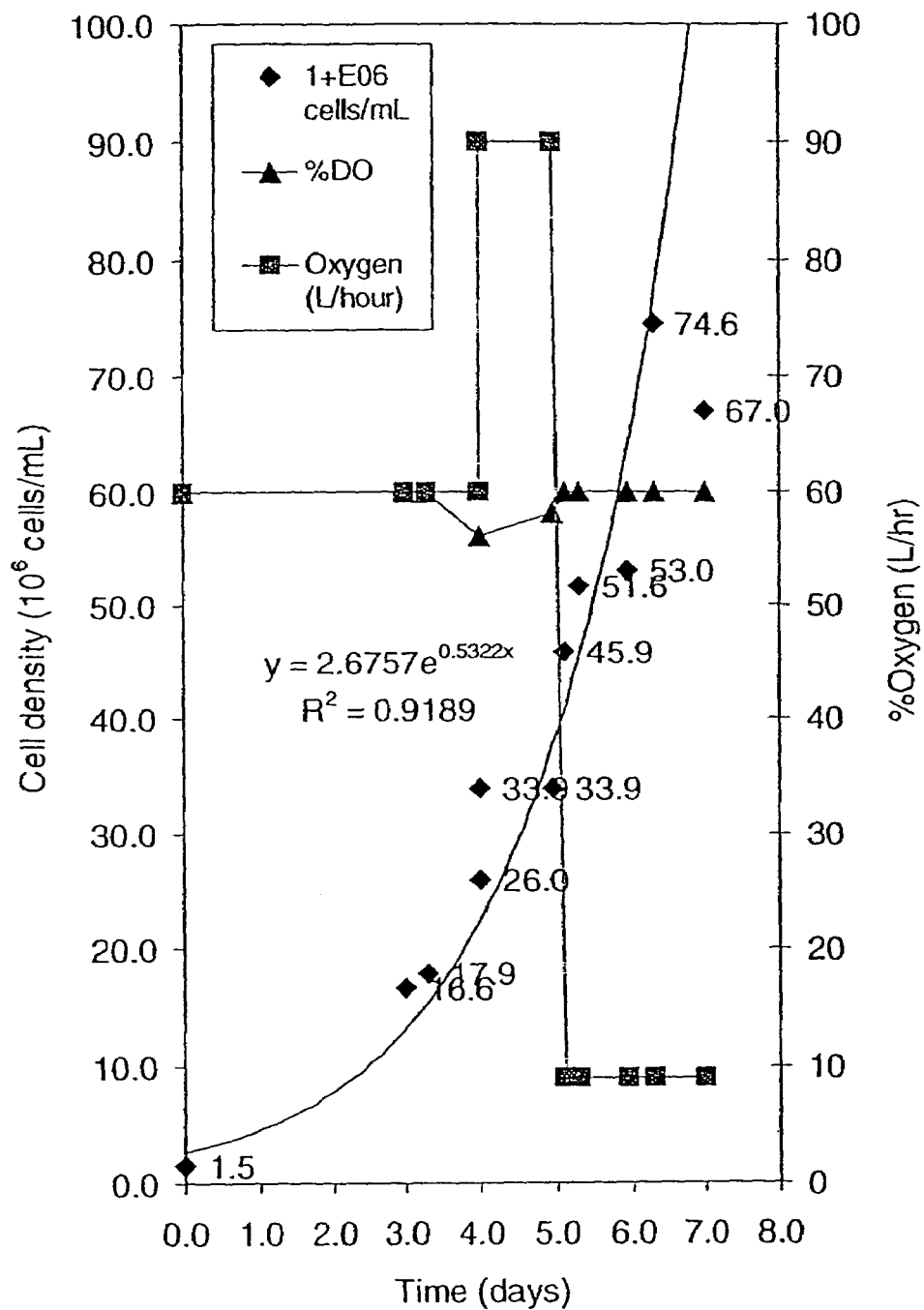

Figure 6. Yields of AcNPV Polyhedrin Protein in Standard and High-Density Cultures.
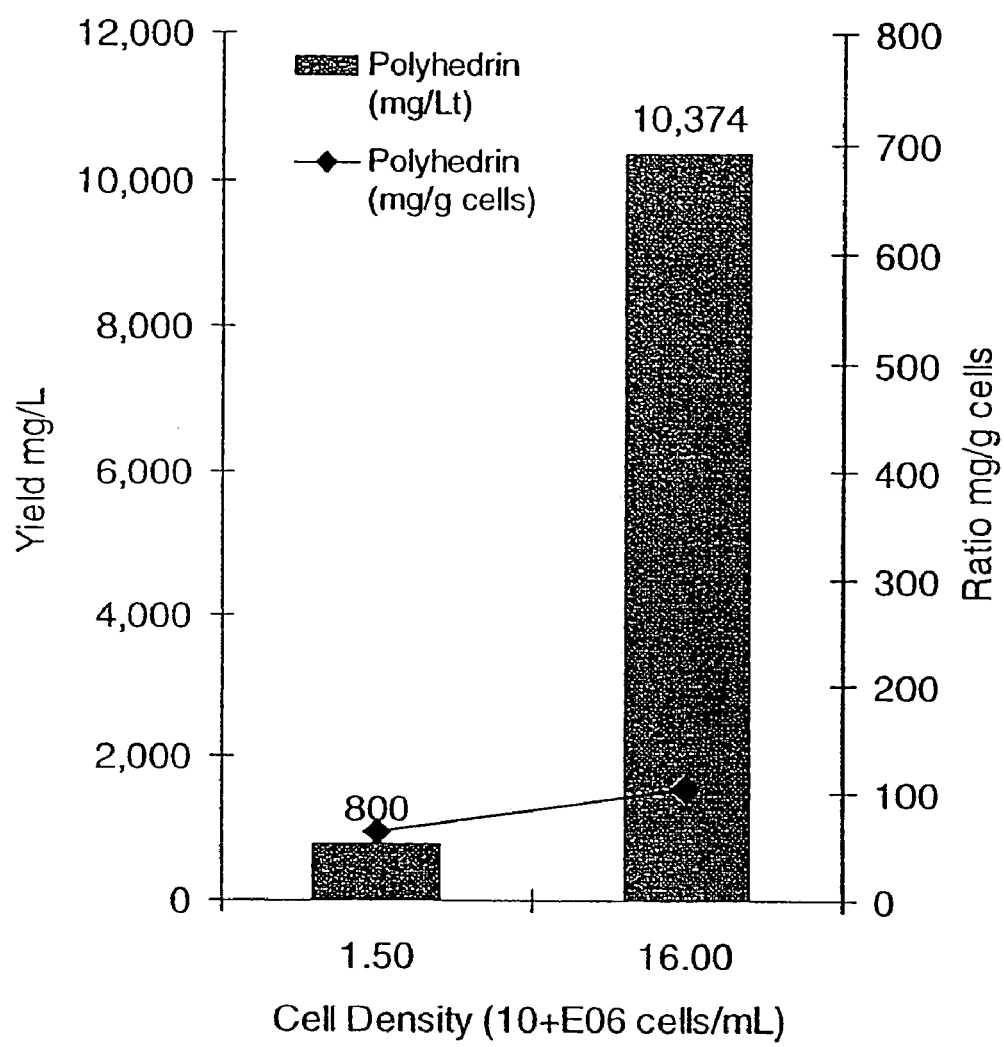

Figure 7 Yields of Recombinant Hemagglutinin from three Strains of Viral Influenza in Standard and High-Density Cultures.

Figure 9

HD Bioreactor Diagram Legend

100 Cell Culturing Loop

- 110 — Stirred-tank Bioreactor
  - 111 — Bioreactor headplate
  - 112 — Cell take-up & cell take-up lines (112a – b)
  - 113 — Cell return & cell return lines (113a – b)
  - 114 — Probe ports: multiple (114a – 114e)
  - 115 — Sampling port
  - 116 — Vent tube
  - 117 — Sparging tube
- 120 — Pump
- 130 — Three-way valve & three-way valve line (130a)
- 140 — Three-way valve & three-way valve line (140a)
- 150 — Oxygenation Loop
  - 151 — Oxygenator & oxygenator Lumen (151a)
  - 152 — Lumen input
  - 153 — Lumen outflow
  - 154 — Gas input
  - 155 — Gas ouput
  - 156 — Selenoid

200 Medium Replenishment Loop

- 210 — Media reservoir
  - 211 — Media container
  - 212 — Media take-up
  - 213 — Media return
  - 214 — Vent tube
  - 215 — Magnetic stir bar
  - 216 — Variable speed magnetic motor
- 220 — Pump
- 230 — "Extraction" loop and "extraction" loop lines (230a – c)
  - 231 — Three-way valve: pass-through or bypass in-line analysis
  - 232 — Three-way valve: collection or sampling
  - 233 — Three-way valve: pass through or return
- 240 — Three-way valve – sampling & three-way valve – sampling line (240a)
- 250 — Media take-up lines (250 & 250a)
- 260 — Media return lines (260 & 260a – c)

300 Hollow Fiber Dialysis Device

- 301 — Lumen input
- 302 — Lumen outflow
- 303 — Extra-lumenal input
- 304 — Extra-lumenal outflow
- 310 — Lumen space
- 320 — Extra-lumen space

|  | Cell/ml x 10E6 | |
| --- | --- | --- |
| Days | High density bioreactor (2L) | Control flask (0.1 L) |
| 0 | 0.9 | 0.9 |
| 1 | 1.3 | 1.8 |
| 2 | 2.4 | 3.0 |
| 3 | 4.3 | 4.6 |
| 4 | 7.8 | 4.1 |
| 5 | 13.6 | |

… # APPARATUS AND METHODS FOR PRODUCING AND USING HIGH-DENSITY CELLS AND PRODUCTS THEREFROM

RELATED APPLICATIONS

Reference is made to, and this application claims priority from, U.S. application Ser. No. 60/162,354, filed Oct. 29, 1999 and U.S. application Ser. No. 60/118,816, filed Feb. 5, 1999, each of which is hereby incorporated herein by reference; and, each document cited in those applications ("U.S. Ser. No. 60/118,816 appln cited document" and "U.S. Ser. No. 60/162,354 appln cited document"), and each document cited or referenced in each U.S. Ser. No. 60/118,816 appln cited document and in each U.S. Ser. No. 60/162,354 appln cited document, is hereby incorporated herein by reference.

Reference is made to U.S. application Ser. No. 08/965,698, filed Nov. 7, 1997, Ser. No. 09/169,178, filed Oct. 8, 1998, Ser. No. 09/372,734, filed Aug. 11, 1999, Ser. No. 09/235,901, filed Jan. 22, 1999, Ser. No. 09/169,027, filed Oct. 9, 1998, Ser. No. 08/120,601, filed Sep. 13, 1993 (allowed), now U.S. Pat. No. 5,762,939, Ser. No. 08/453,848, filed May 30, 1995 (allowed), now U.S. Pat. No. 5,858,368, Ser. No. 09/111,169, filed Jul. 7, 1998, and Ser. No. 08/430,971, filed Apr. 28, 1995 (allowed; U.S. Pat. No. 5,976,552 issued Nov. 2, 1999), each of which is hereby incorporated herein by reference; and, each document cited in each of these applications and patents or during their prosecution (e.g., as shown on the face of the patents or in their file histories) is hereby incorporated herein by reference. For instance, the present invention may be employed in practicing any or all of the aforementioned patent applications or for otherwise expressing exogenous DNA or in producing cells, e.g., for expressing exogenous DNA, for any or all of the aforementioned applications. Similarly, all documents cited in this text ("herein cited documents") and documents referenced or cited in herein cited documents or during the prosecution of any herein cited document (e.g., in the case of a herein cited document being a patent) are likewise incorporated herein by reference.

FIELD OF THE INVENTION

The present invention relates to methods and apparatus for the growth of cells, advantageously to high density, and uses thereof, including uses of the cells; and, products from the methods, apparatus and the cells. The present invention relates to methods and apparatus for the growth of cells, advantageously of high density cells, for expression of exogenous DNA, such as from infection by a viral vector containing the exogenous DNA or by a plasmid transfected and/or inserted into such cells and containing such DNA, and uses thereof, including uses of the cells; and, products from the methods, apparatus and the cells and uses of such products.

The present invention also relates to methods and apparatus for the growth and infection of insect cells, advantageously at high-density, and uses thereof, including uses of the cells; and, products from the methods, apparatus and the cells and uses thereof. Furthermore, the invention relates to methods and apparatus for the production and use of insect cells, advantageously high density insect cells, for infection with wild type and/or genetically engineered recombinant baculoviruses, as well as to methods and apparatus for the production and use of cells, advantageously to high density, for infection, transfection or the like with wild type and/or engineered recombinant vectors, e.g., viruses, plasmids, and uses thereof, including uses of the cells; and, products from the methods, apparatus and the cells and uses thereof.

The methods and apparatus can include at least one bioreactor, advantageously at least one stirred-cell bioreactor, at least one source of culture medium (external to the bioreactor), advantageously at least one source of stirred culture medium (external to the bioreactor), at least one means for circulating media and/or cell culture, and at least one means for dialysis of nutrients and waste (and/or extracellular expression and/or secreted) products between the cells in the bioreactor and the external source of culture medium, such as at least one semi-permeable membrane, e.g., a hollow fiber filter, that results in the dialysis of nutrients and waste (and/or extracellular expression and/or secreted) products between the cells in the bioreactor and culture medium; e.g., whereby there is a first loop between the culture medium source and the dialysis means (media replenishment loop) and a second loop between the bioreactor and the dialysis means (cell culture loop).

The methods and apparatus can include at least one bioreactor, advantageously at least one stirred-cell bioreactor, at least one source of culture medium (external to the bioreactor), advantageously at least one stirred source of culture medium (external to the bioreactor), at least one means for circulating media and/or cell culture, and at least one means for delivery of oxygen, such as at least one oxygenator including input and output ports.

The methods and apparatus can include at least one bioreactor, advantageously at least one stirred-cell bioreactor, at least one source of culture medium (external to the bioreactor), advantageously at least one source of stirred culture medium (external to the bioreactor), at least one means for circulating media and/or cell culture, at least one means for dialysis of nutrients and waste (and/or extracellular expression and/or secreted) products between the cells in the bioreactor and the external source of culture medium, such as at least one semi-permeable membrane, e.g., a hollow fiber filter, that results in the dialysis of nutrients and waste (and/or extracellular expression and/or secreted) products between the cells in the bioreactor and culture medium, e.g., whereby there is a first loop between the culture medium source and the dialysis means (media replenishment loop) and a second loop between the bioreactor and the dialysis means (cell culture loop), and optionally but advantageously present, means for delivery of oxygen; for instance, via means comprising at least one oxygenator including input and output ports. Advantageously, oxygen is delivered in a way such that proper oxygenation of the cells is maintained at cell densities especially at high densities. A "source of culture medium" or "culture medium source" can be a vessel for culture medium. A bioreactor can be a vessel for cells or cell culture.

Further, the methods and apparatus can include means for the delivery of other gases, such as air, and/or nitrogen, and/or carbon dioxide. The methods and apparatus also can include means for monitoring of chemical and/or physical parameters, such as pH and/or conductivity and/or temperature and/or oxygen concentration and/or carbon dioxide concentration and/or nitrogen concentration and/or glucose/nutrient concentration. And, the methods and apparatus can include means for adjusting one or more chemical and/or physical parameters of the system such as a function of one or more monitored parameters, e.g., pH and/or temperature and/or oxygen concentration and/or carbon dioxide concentration.

The methods and apparatus can optionally include means for monitoring and/or probing the system such as probe port(s); and further optionally means for delivery of at least one additional gas such as air and/or nitrogen and/or carbon dioxide; and still further optionally means for monitoring and/or regulating other parameters such as pH and/or temperature.

Accordingly, the invention can relate to a method for growing cells comprising culturing cells in at least one bioreactor whereby there is a cell culture, supplying medium in at least one vessel whereby there is culture medium, circulating culture medium and/or cell culture, whereby the bioreactor and vessel are in fluid communication and the cell culture and/or culture medium are in circulation, and delivering oxygen to the cell culture and/or culture medium.

And, the invention also can relate to a method for growing cells comprising culturing cells in a bioreactor whereby there is a cell culture, supplying culture medium in a vessel where by there is culture medium, circulating the cell culture through a dialysis means, circulating culture medium through the dialysis means, wherein the dialysis means in fluid communication with the bioreactor and the vessel, whereby there is a first, cell culture, loop between the bioreactor and the dialysis means, and a second, media replenishment, loop between the vessel and the bioreactor, and the method includes performing dialysis between the culture medium and the cell culture.

Other aspects of the invention are described in or are obvious from (and within the ambit of the invention) the following disclosure.

BACKGROUND OF THE INVENTION

Biological substances derived from animal cell cultivation are finding uses in a variety of medical and agricultural applications. The importance of recombinant proteins, a specific subset of biological substances, has been the basis for many new and emerging therapies and diagnostic methodologies ranging from vaccines to cancer therapies.

Cell culturing processes for the production of biological substances range in complexity from simple manually operated batch processes to complex computer controlled continuous cultivation bioreactors; for instance, from simple 50 mL spinner flasks to complex stirred-tank bioreactors of 500 L or more with automatically operated multiple measurement devices and feedback controls. The basic principle behind each process is to utilize cells as catalytic engines to produce useful biological substances such as viruses or proteins using medium in which the cells are bathed to provide both a source of required nutrients and a means of removing inhibitory waste material.

As the production of biological substances moves from the research laboratory to commercial production, competitive markets demand productivity improvements. The yield of product from each commercial bioreactor becomes critical. So to with quality, the market demands reliability and consistency of output. Current cell culturing processes readily reach their limiting conditions for production of biological substances. These limitations are imposed by the nutrient and oxygen requirements of the cells and by accumulation of inhibitory waste metabolites; and are reached well before the theoretical limits of cell growth or protein production are reached.

Not all cell types are capable of producing all biological substances. Many biological substances found in certain cells are incompatible with or even toxic to other cell types. The choice of cell types in many situations depends on the structural complexity of the end protein being produced. While protein production levels are high in prokaryotic organisms given their rapid growth and concomitant high levels of protein expression, they are not always capable of producing functional proteins as they perform no or incomplete or different post-translational and/or co-translational modifications such as glycosylation, phosphorylation and complex multi-unit macro-assembly.

Animal cells do perform the necessary complex post-translational modifications including glycosylation, phosphorylation and macro-assembly. However, some animal cells, especially mammalian cells, are difficult to grow and maintain and do not readily lend themselves to high yield production of biological substances under industrial conditions. As a subset of animal cells, insect cells are capable of glycosylation, phosphorylation and macromolecular assembly. For the production of many recombinant proteins, insect cells are an excellent choice because these cells have simple growth requirements, are highly susceptible to infection by recombinant baculoviruses engineered to produce biological substances in insect cells, and have a good safety profile.

Cell types and desired growth dynamics dictate the selection of a bioreactor type. Basic bioreactor devices include culture flasks, roller bottles, shaker flasks, stirred-tank reactors, air-lift reactors and more recently, hollow fiber reactor devices. There are advantages and disadvantages to each type of bioreactor and these advantages and disadvantages vary according to the type of cell cultured in the system and the specific properties of those cells. What works well with attached cells may not with suspended cells. Therefore, improved bioreactors need to be flexible. They should support various cell types, operate for short or long duration cultivation periods and should operate at scales ranging up to 10,000 liters.

Growth of attached cells is limited to the surface area available and when roller bottles are used, scale up of attached cell production of biological substances can demand significant amounts of space. Alternatively, for attached cells, microcarriers can be used. However, these can limit nutrient and oxygen availability to the cells and often expose them to additional sheer forces as the use of microcarriers requires a stirred tank. Additionally, matching the proper microcarrier type to the specific cell type can prove difficult.

Insect cells represent an economically important cell type with demonstrated usefulness in manufacturing biological substances. Typically, insect cells are cultured as suspensions in stirred cell bioreactors.

Unlike bacteria that are enclosed in cell walls, animal cells, and specifically insect cells, respond negatively to relatively mild hydrodynamic shear forces found in an operating bioreactor. These damaging events include bulk-fluid turbulence associated with spinner vortex formation, fluid-tank wall collisions and gas/liquid interfaces. This gas/liquid interfaces include the interface between the culture medium and head space gas with the stirred tank and between culture medium and oxygen bubbles formed during oxygen addition, such as with sparging. Insect cells are more sensitive than many other animal cells to these hydrodynamic shear forces (Wu J, King G, Daugulis A. J., Faulkner O, Bone D. H., Goosen M. F. A. (1989) *Applied Microbiology and Biotechnology* 32: 249). Compounding this sensitivity is the requirement of insect cells for higher oxygen levels: introduction of oxygen produces more bubbles, that is, more gas/liquid interface, and the opportunity for more hydrodynamic shear damage.

Thus, with insect cells, the mechanism for adding oxygen to the system becomes critical. First, the cells are more sensitive to the shear forces than are other animal cells. Second, more oxygen is required to grow these cells than is required to grow other animal cells. This additional oxygen requirement brings with it the probability of further cell destruction associated with increased bubbling from the higher oxygen supply and with faster stirring required to ensure even oxygen distribution. And third, when infected with baculovirus, the oxygen demand increases yet again and so too, the probability for shear related damage increases with a third factor.

Cell death is the end result of excessive shear forces, resulting from loss of membrane integrity, cell lysis, and altered metabolic activity. This insect cell sensitivity to shear forces related to high oxygen requirement is evidenced by the need for surfactant addition to the culture medium in sparged stirred tank bioreactors of any size (Murhammer D. W., Goochee C. F. (1990) *Biotechnology Progress* 6: 391).

During the cell culturing processes, oxygen demand increases as cell density increases. If the oxygen need is met through increased oxygen flow and stirring, shear forces increase. Thus, oxygen remains one the of key limiting factors in high density cell culture due to the need to limit shear related cell death. In turn, limiting oxygen addition restrains cell growth and makes high density culture unattainable. Furthermore, poor oxygenation directly limits output of recombinant protein with insect cell based cell culturing systems.

Thus, it would be an advance in the art to address issues that limit cell density and recombinant protein production, such as providing both a source of required nutrients and a means of removing inhibitory waste material and/or providing oxygenation that addresses the desire to reduce or limit shear related cell death from oxygenation.

Zhang et al. Biotech. Bioeng. 59(3): 351-9 (1998) relates to a high-density insect cell perfusion process utilizing an ultrasonic filter device as a means to retain cells within the bioreactor while extracting spent medium. Per cell yields of recombinant protein were similar between normal conditions (when cells were diluted to a low density and infected with a genetically engineered baculovirus) and high-density conditions, and thus failing to demonstrate, show, teach or suggest production of a recombinant protein at high cell density. And, in a perfusion system, nutrients and waste never approach equilibrium. Thus, Zhang et al. either individually or in any combination fails to teach or suggest the present invention.

Likewise, any other filters or hollow fibers or hollow fiber filter devices or uses thereof fail to teach or suggest the present invention. For instance, in contrast with certain embodiments of the present invention, filters or hollow fibers or hollow fiber filter devices can be used: by removing medium and the cells from the bioreactor vessel, passing it through the filtering device, collecting the perfused fluid containing the desired biological substance and returning the medium with its cells to the original bioreactor vessel; or as housing for cells of interest within the extra-lumenal space of a hollow fiber filter device with perfused medium passed through the capillary tubes to the cells; or by placing unencased hollow fibers directly into the fermentation tank itself so that fresh medium can be more directly provided to immobilized or attached cells.

Microbead encapsulation involves porous hollow microballoons. Culture cells attach to the internal surfaces of these porous hollow microballoons. By controlling the diameter of the microballoon and its pore sizes, relative to cell size, the thickness of the cell layers can be controlled to allow for adequate delivery of nutrients and removal of waste metabolites. Microbead encapsulation fails to teach or suggest the present invention.

Spaulding et al., U.S. Pat. No. 5,637,477, concerns a process for insect cell culture that reduces shear, in a horizontally rotating culture vessel. Spaulding et al. too, either individually or in any combination fails to teach or suggest the present invention.

Goffe, U.S. Pat. No. 5,882,918 relates to a cell culture incubator. There is no circulation of cells. Goffe, either individually or in any combination, fails to teach or suggest the present invention.

Portner et al. Appl Micro Biot. 403-414 (1998) is directed to dialysis cultures and involves a complicated dialysis process coupled with the perfusion of waste and the addition of nutrient concentrate(s) as a means to reach high cell densities wherein the removal of waste is done in a dialysis vessel connected to a semi-permeable membrane and two additional vessels (one for the addition of dialyzing fluid and the second for the removal of waste). As a result, some nutrients must also dialyze into the dialysis vessel and get wasted. Further, one or more concentrates are added directly to the culture vessel to add nutrients and support the growth of cells and to replace what is being lost in the dialysis compartment of the bioreactor.

Portner et al. state that a limitation of their design when used in a stirred tank bioreactor is oxygen limitation in their dialysis loop (p. 409). Further, in one example with mammalian cells (p. 410, hybridoma cells), Portner et al. give no data or any indication that cells actually grew to high density; and in fact, the yields of monoclonal antibodies they report after 850 hours of culture (35.4 days) were relatively low (478 mg/l or 13.8 mg/day). Further, Portner state in their conclusions (p. 412) that their dialysis bioreactor can be used with stationary animal cells and that for large-scale cultures of suspended cells, that an external loop can "lead to severe problems, mainly due to oxygen limitations in the loop."

Thus, Portner et al. directly teach away from the present invention by directly teaching that a bioreactor with an external loop of circulating cells will not work. Moreover, Portner relates to the use of an open bioreactor system requiring constant addition of dialyzing fluid to a dialysis chamber and nutrient concentrates to the bioreactor. Continuous perfusion of the dialysis chamber is a variation on a perfusion system in which nutrients and waste never approach equilibrium. And, Portner et al. do not teach or suggest the addition of oxygen by in line sparging or other means, suggesting that external circulation of cells is limited by oxygen depravation.

Garnier et al., Cytotechnology 22:53-63 (1996) relates to dissolved carbon dioxide accumulation in a large scale and high density production of $TGF\beta$ receptor with baculovirus infected Sf-9 cells: Aeration apparently involved accumulation of dissolved carbon dioxide that inhibited protein production; oxygen may serve as a carrier gas for desorbing carbon dioxide. Garnier used a low flow rate of pure oxygen with a dissolved oxygen content of 40%, and shows that there was a problem in the art, namely that higher rates of oxygen addition can result in hydrodynamic stress detrimental to the culture. Garnier fails to teach or suggest how one could provide higher rates of oxygen transfer, or to balance oxygen transfer, mechanical stress and carbon dioxide, inter alia. Garnier fails to teach or suggest the addition of oxygen by in line sparging or other means of the present invention, as well as the apparatus and methods of the present invention, inter alia.

Karmen et al. Biotechnology and Bioengineering 50:36-48 (1996) is directed in on-line monitoring of respiration in recombinant-baculovirus infected and uninfected insect cell bioreactor cultures. Dissolved oxygen (DO) levels were generally at about 40%, and as to DO, the authors assert that further investigations are required to clarify the effect of DO on baculovirus-infected insect cells. Karmen et al. may provide that resperation in insect cell cultures can be continuously monitored on-line with data from an $O_2$ control system or an IR $CO_2$ detector; but, fails to teach or suggest the system and apparatus of the present invention, especially the addition of oxygen by in line sparging or other means of the present invention (alone or in combination with dialyzing means), dialyzing means (alone or in combination with oxygen addition means) as in the present invention as well as other apparatus and methods of the present invention, for instance, use or adjusting of $CO_2$ in response to pH changes inter alia (and indeed, Karmen teaches away from such by reporting that insect cell cultures reportedly do not require $HCO_3^-/CO_2$ buffering).

Nakano et al. Appl Microbiol Biotechnol 48(5):597-601 (1997) relates to the infuence of acetic acid on the growth of *E coli* during high-cell density cultivation in a dialysis reactor with controlled levels of dissolved oxygen with different carbon sources (glucose and glycerol); but fails to teach or suggest methods and apparatus of the invention.

Gehin et al. Lett Appl Microbiol 23(4):208-12 (1996) concerns studies of *Clostridium cellulolyticum* ATCC 35319 under dialysis and co-culture conditions. This was in batch with and without pH regulation. $H_2$, $CO_2$ acetate, ethanol and lactate were end-products. No synergistic action was found. Methods and apparatus of the invention are not taught or suggested by Gehin.

Schumpp et al. J Cell Sci 97(Pt4):639-47 (1990) relates to culture conditions for high cell density proliferation of HL-60 human promyelocytic leukemia cells. While nutrient supply and metabolic end product accumulation are possible growth limiting factors, Schumpp favors a perfusion method. Accordingly, methods and appartus of the invention are not taught or suggested by Schumpp.

LaIuppa et al., "Ex vivo expansion of hematopoietic stem and progenitor cells for transplantation," in Jane N. Winter (ed.), Blood Stem Cell Transplantation, 1997 illustrates various systems for expansion of hematopoietic stem and progenitor cells, and fails to teach or suggest methods and apparatus of the invention.

Bedard et al., Biotechnology Letters, 19(7):629-632 (July 1997) concerns fed batch culture of Sf-9 cells which reportedly supported $3\times10^7$ cells per ml and improved baculovirus-expressed recombinant protein yields; and relates to Sf-900 II medium and nutrient additives and nutrient concentrates. While medium, additives and nutrient concentrates may be employed in the practice of the herein invention, Badard et al. fails to teach or suggest methods and apparatus of the invention. Indeed, more generally, while components and/or cells found in literature, such as herein cited literature, may be employed in the herein invention, it is believed that heretofore methods and appartus of the invention have not been taught or suggested.

Accordingly, it is believed that heretofore simple systems, e.g. closed systems, as in the present invention, where, for instance, nutrients and waste products in the bioreactor and the dialysate are in equilibrium and do not necessitate continuous perfusion (dialysis used not only for removal of waste but for addition of nutrients) and/or the issue of oxygen depletion is addressed, e.g., by the addition of oxygen directly to circulating cells, with also the issue of reducing or limiting shear related cell death due to oxygenation by reducing or limiting or eliminating shear forces from oxygen addition addressed, have not been taught or suggested. And, it is believed that heretofore, new bioreactor systems and apparatus for high-density cell growth, uses thereof, products therefrom, as described and claimed herein, as well as the herein methods for making and using such a high-density cells and products therefrom, have not been disclosed or suggested in the art.

OBJECTS AND SUMMARY OF THE INVENTION

An object of the invention can be to provide an apparatus and/or a process for the growth of cells and/or of cell products, for instance, to high density.

The apparatus and process can include the use of a dialysis procedure for the simultaneous removal of waste products and the replacement of nutrients during the growth of cultured cells. The dialysis procedure can employ the circulation of the growing cells through a semi-permeable membrane, such as a hollow fiber filter, where there is the exchange of small molecules between the cell medium and an external source of addition medium, referred to as 'regeneration' medium or media. Semi-permeable membranes permit the passage of water and small molecules and smaller proteins but not cells. If the concentration of a small molecule increases or decreases on either side of the membrane, then the concentration gradient leads to the exchange of molecules across the semi-permeable membrane. This provides for removal of waste molecules out of the cell compartment along a concentration gradient and entry of replacement nutrients into the cell compartment along a different concentration gradient. Where the membrane is essentially inert, as in a hollow fiber filter, then the movement is driven by the diffusion of molecules across the membrane and requires no specific pressurization to drive the molecules across the membrane.

The apparatus and process can provide a modular set of interchangeable components. This interchangeability can provide for optimization during different phases of a cell cultivation run to improve performance and for the capability for rapidly exchanging a malfunctioning component without aborting a cell cultivation run.

The circulation of cells through the relatively small diameter tubing of the hollow fiber filter provides the additional advantage of disrupting any clumped cells. Clumped cells are not as efficient in producing product since the interior cells of a clump cannot as easily absorb nutrients and oxygen and eliminate waste products as the outer cells.

Another object of the invention can be to provide an apparatus and a process for the addition of oxygen to growing cells using a novel procedure where the addition of oxygen is done outside the bioreactor and into a circulating loop of cells. This process is referred to as 'in-line' oxygenation. A means of introducing the oxygen gas is to circulate the cells through a hollow fiber filter designed for the addition of oxygen to fluid, such as the UniSyn Technologies Oxy 1. Alternatively and/or additionally, oxygenation can be accomplished by direct sparging of the circulating loop of cells and/or with isolated fibers within the hollow fiber filter device used in medium exchange dedicated to oxygen exchange and/or through sparging of the "replenishment" medium and/or through at least one oxygen-containing compound that releases dissolved oxygen and/or any combination of these oxygenation means.

An embodiment of the invention is the use of insect cells in a process that provides for their growth to high density; however, the invention is applicable to any cells, e.g., typical cells used in expression systems (see infra).

A further object of the invention can be to use cells, such as insect cells or cells used in expression systems at high density with any, or all, and advantageously most or all, of the following characteristics: replicate continuously in suspension as single cells, making them ideal for use in large-scale pharmaceutical bioreactors; grow to high density with a high degree of viability in a low-cost, serum-free medium; support the replication of vectors, e.g., baculoviruses, to high titers;

when infected with a genetically engineered recombinant vector, e.g., baculovirus, gene; produce products at high levels and produce those products consistently over many passages; meet all regulatory requirements for identity and safety; readily expand to large-scale bioreactors for the manufacture of pharmaceutical products; and, store and culture in a serum-free medium.

Yet another object of the invention can be to provide a bioreactor and a process which overcomes or addresses at least one or more problem(s) of prior bioreactors and processes, e.g., problems identified herein with prior high-density bioreactor processes.

Surprisingly it has been found that the herein apparatus and process will grow cells such as insect cells or cells used in expression systems to high density and make them ideal for use in the large-scale production of gene products for use in human and animal health. At high cell density, the cells grow continuously as single cell suspensions in a commercial serum-free medium, divide rapidly and maintain a high level of viability, and are highly permissive for infection or transfection with vectors, e.g., baculoviruses, producing high virus titers and high levels of recombinant gene products. In addition, the herein bioreactor and process can be used with Sf900+ insect cells that meet the requirements for identity and safety recommended for the manufacture of recombinant DNA gene products under the U.S. current Good Manufacturing Practices (cGMP) specifications (Code of Federal Regulations 21, Part 211, Current Good Manufacturing Practice for Finished Pharmaceuticals, Apr. 1, 1995). The Sf900+ cells are also in compliance with the guidelines issued by the U.S. Food and Drug Administration Points to Consider for Cell Lines used in the Production of Pharmaceutical Products (Points to Consider in the Characterization of Cell Lines Used to Produce Biologicals, issued May 17, 1993, U.S. Food and Drug Administration, Rockville, Md.).

Thus, an embodiment of this invention can be a process for the growth of cells, e.g. the insect cells Sf900+, to high cell densities.

Another object of the invention can be to provide different media during the course of cell culture. The purpose is to change medium composition during different phases of cell culture to optimize nutrient utilization. For example, a "growth" media would be optimized for growth of cells to high density while an "expression" media would be optimized for the expression of biological substances in the cells. It can be a further object of the invention that the "expression" media be a low cost formulation composed of carbohydrates and organic and inorganic salts. This media thus reduces the cost of production of a biological substance. Additionally, since more complex media often contain substances that are difficult to separate from the desired product, simple "expression" medium allows for easier purification, reducing cost yet again.

Another embodiment of this invention can be to provide a method to use the high-density cells for the production of high titers of wild type and genetically engineered recombinant vectors, e.g., baculoviruses.

Yet another embodiment of this invention can be to provide the use of the bioreactor and process to produce high density cells to make vectors, e.g., expression vectors, such as baculovirus expression vectors, and to produce high-titer stocks of recombinant virus or vector suitable for use in the production of recombinant gene products.

Still another embodiment of this invention can be to provide the bioreactor and process to produce cell lines conforming to standard tests for identity and safety, whereby the cells can be used in the commercial manufacture of pharmaceutical products.

And, another embodiment of this invention can be to provide a bioreactor and method for the production of cells such as insect cells for large-scale commercial production of recombinant gene products from expression vectors such as baculovirus expression vectors.

The inventive bioreactor and process for high cell density is especially suited for practicing the teachings of the applications and patents above-referenced under "Related Applications"; and, this provides yet further embodiments of the invention.

Accordingly, in certain aspects, the invention can entail apparatus and process for producing high densities of cells. The invention, in certain aspects, can also comprehend the use of a high density process for the growth of an insect cell line such as an insect cell line established from Lepidoptera, Noctuidae, *Spodoptera frugiperda* Sf900+ (ATCC: CRL 12579) in a serum-free insect medium supplemented. The invention, in certain aspects, can also comprehend an expression system such as a baculovirus expression system, including a recombinant virus or vector, e.g., baculovirus, that includes exogenous coding DNA, wherein cells such as insect cells, at high density from inventive apparatus and methods are infected or transfected with the recombinant vector or virus, e.g., baculovirus.

Further, the invention provides an apparatus for growing cells comprising at least one bioreactor for cell culture, at least one vessel for culture medium, means for circulating culture medium and/or cell culture, whereby the bioreactor and vessel are in fluid communication, and at least one means for delivery of oxygen. The invention further provides an apparatus comprising a bioreactor for cell culture, a vessel for culture medium, means for circulating cell culture, means for circulating culture medium, dialysis means in fluid communication with the bioreactor and the vessel, whereby there is a first, cell culture, loop between the bioreactor and the dialysis means, and a second, media replenishment, loop between the vessel and the bioreactor, and in operation dialysis between the culture medium and the cell culture; and, this apparatus can further comprise at least one means for delivery of oxygen into the cell culture loop.

The means for delivery of oxygen comprises a hollow fiber filter oxygenator and/or means for delivery of oxygen comprises means for in-line sparging and/or means for delivery of oxygen comprising means for delivery of at least one oxygen-containing compound that releases dissolved oxygen into cell culture. The means for delivery of oxygen can be positioned upstream of input of circulating cell culture returning to the bioreactor. The bioreactor and/or the vessel; and advantageously both the bioreator and the vessel, are stirred. The means for delivery of oxygen can provide an average dissolved oxygen concentration of about 60% and/or greater than 60% or 65%; and/or the means for delivery of oxygen can provide an average dissolved oxygen concentration of greater than about 40% and/or the means for deliver of oxygen can provide an average dissolved oxygen concentration between about 30% and 90% or between about 40% and about 80% or between about 50% and 70%.

The apparatus can further comprise means for measuring physical and/or chemical parameters of the cell culture and/or the culture medium; for instance, in the cell culture loop and/or the media replenishment loop, such as probes or sensors in the bioreactor or the vessel or at any suitable point in the loop(s) (for instance, where there is withdrawal from the loops such as for sampling). The means for measuring can comprise means for measuring dissolved oxygen concentration; e.g., in the cell culture or cell culture loop, for instance, a probe or sensor in the bioreactor for detecting dissolved oxygen in the cell culture therein. The means for measuring can comprise means for measuring pH; e.g., in the cell culture or cell culture loop, for instance, a probe or sensor in the bioreactor for detecting pH. The means for measuring can comprise means for measuring temperature; e.g., in the cell culture or cell culture loop, for instance, a probe or sensor in the bioreactor for detecting temperature. The means for measuring can comprise means for measuring pH and means for measuring dissolved oxygen; e.g., in the cell culture or cell culture loop, for instance, probes or sensors in the bioreactor for detecting each of pH and dissolved oxygen. The means for measuring can comprise means for measuring and/or counting cell density or cells.

The apparatus can further comprise means for adjusting physical and/or chemical parameters of the cell culture and/or the culture medium in response to data from the measuring means. The adjusting means can comprises means to adjust temperature, such as a heating and/or cooling jacket in surrounding relationship with the vessel and/or the biorector connected to a computer, microprocessor or processor that provides a signal to the jacket for heating and/or cooling in response to temperature measurements varying from a desired level. The adjusting means comprises means for adjusting pH; such as means for adding a chemical to the cell culture and/or the media that alters pH therein connected to a computer, microprocessor or processor that provides a signal to the adjusting means for addition of the chemical in response to pH measurements varying from a desired level, for instance, means for adding carbon dioxide to the cell culture in response to pH measurements. Thus, the adjusting means also can comprise means for adjusting dissolved carbon dioxide concentration. Further, the adjusting means can comprise means for adjusting dissolved oxygen concentration; for instance, means for addition of oxygen and/or air (or both) in response to oxygen measurements varying from a desired level (such as a level between 30% and 90% such as between 40% and 80% for instance between 50% and 70%, e.g., approximately 60%). In addition and/or alternatively, the adjusting means can call for adjusting and/or changing conditions in response to a cell density and/or cell count measurement; for instance, at a particular cell and/or cell count, media may be changed and/or a vector (e.g., recombinant virus such as baculovirus) added for infection.

Advantageously, the adjusting means comprises means for adjusting dissolved oxygen and means for adjusting dissolved carbon dioxide, whereby in response to pH measurement(s), dissolved carbon dioxide levels are adjusted; and, even more advantageously, the adjusting means also includesmeans for adjusting dissolved oxygen in response to dissolved oxygen measurement(s). These "adjustments" are advantageously performed in the cell culture loop; e.g., addition of carbon dioxide and oxygen are performed in the cell culture loop, for instance, at the oxygenator. The pH can be set to a desired level and carbon dioxide adjusted when pH varies from the desired level, whereby the dissolved oxygen measurement varies periodically as a function of time. For instance, the dissolved oxygen measurement varies from 30% to 90% or from 40% to 80% or from 50% to 70%; or, the dissolved oxygen measurement averages about 60% and/or the dissolved oxygen measurement can vary from high value to low value over about 10 to about 30 minutes or over about 20 minutes and/or a plot of the dissolved oxygen measurement as a function of time comprises a sin wave.

The invention yet further comprehends methods involving the inventive apparatus or steps performed by the apparatus or analogous apparatus.

The invention still further provides a method for growing cells comprising culturing cells in at least one bioreactor whereby there is a cell culture, supplying medium in at least one vessel whereby there is culture medium, circulating culture medium and/or cell culture, whereby the bioreactor and vessel are in fluid communication and the cell culture and/or culture medium are in circulation, and delivering oxygen to the cell culture and/or culture medium. The invention also provides a method for growing cells comprising culturing cells in a bioreactor whereby there is a cell culture, supplying culture medium in a vessel where by there is culture medium, circulating the cell culture through a dialysis means, circulating culture medium through the dialysis means, wherein the dialysis means in fluid communication with the bioreactor and the vessel, whereby there is a first, cell culture, loop between the bioreactor and the dialysis means, and a second, media replenishment, loop between the vessel and the bioreactor, and the method includes performing dialysis between the culture medium and the cell culture.

The delivering of oxygen can be by means for delivery of oxygen comprising a hollow fiber filter oxygenator and/or by means for in-line sparging and/or for delivery of at least one oxygen-containing compound that releases dissolved oxygen into cell culture; and, oxygen can be delivered into the cell culture and/or the cell medium; advantageously into the cell culture; for instance, into the cell culture loop, such as immediately prior to return of cell culture to the bioreactor, e.g., upstream of input of circulating cell culture returning to the bioreactor.

The method can further comprise stirring the cell culture or the culture medium or, advantageously, both the cell culture and the culture medium.

The delivering of oxygen can provide an average dissolved oxygen concentration of about 60% or greater than about 60% or greater than about 65%; and/or an average dissolved oxygen concentration of greater than about 40%; and/or the delivering of oxygen can provide an average dissolved oxygen concentration between about 30% and 90% or between about 40% and about 80% or between about 50% and 70%.

The dialysis means can comprise at least one semi-permeable membrane. The semi-permeable membrane can comprise at least one hollow fiber filter.

Furthermore, the methods can include delivering oxygen into the cell culture loop; for instance, the delivering of oxygen can be by means for delivery of oxygen comprising a hollow fiber filter oxygenator and/or by means for delivery of oxygen comprising means for in-line sparging and/or the delivering of oxygen can comprise delivering at least one oxygen-containing compound that releases dissolved oxygen into cell culture. The delivering of oxygen can by means for delivery of oxygen is positioned upstream of input of circulating cell culture returning to the bioreactor.

Further still, the methods can include measuring physical and/or chemical parameter(s) of the cell culture and/or the culture medium. The measuring can comprise measuring dissolved oxygen concentration and/or measuring pH and/or measuring temperature; and/or measuring pH and measuring dissolved oxygen concentration and/or measuring cell density and/or amount of cells.

Even further still, the methods can include adjusting physical and/or chemical parameters of the cell culture and/or the culture medium (advantageously the cell culture) in response to data from the measuring; for instance, the methods can include adjusting temperature to maintain a desired temperature and/or adjusting pH to maintain a desired pH and/or adjusting dissolved oxygen concentration to maintain a desired dissolved oxygen concentration and/or adjusting dissolved carbon dioxide concentration. The methods can include adjusting dissolved oxygen concentration and adjusting dissolved carbon dioxide concentration, whereby in response to pH measurement(s), dissolved carbon dioxide levels are adjusted; and/or adjusting dissolved oxygen levels in response to dissolved oxygen measurement(s). The methods can include adjusting pH to a desired level in response to pH measurements by adjusting the dissolved carbon dioxide concentration such that dissolved carbon dioxide concentration is adjusted when pH varies from the desired level, and the dissolved oxygen measurement varies periodically as a function of time. The methods can include adjusting the dissolved oxygen concentration so that the dissolved oxygen measurement varies from 30% to 90% or from 40% to 80% or from 50% to 70%; or, so that the dissolved oxygen measurement averages about 60% and/or adjusting the dissolved oxygen concentration so that the dissolved oxygen measurement varies from high value to low value over about 10 to about 30 minutes or over about 20 minutes and/or a plot of the dissolved oxygen measurement as a function of time comprises a sin wave. Additionally or alternatively, the adjusting can be an adjustment of conditions in response to cell density and/or cell count measurement; for instance, media can be added and/or changed and/or a vector (e.g., recombinant virus such as baculovirus) added for infection in response to the cell density and/or cell count measurement.

Yet further still, the methods can include collecting the cells. The invention thus comprehends methods for producing cells. The invention even further comprehends wherein the cells contain a vector. Thus, the invention also comprehends methods for replication of the vector and/or expression of exogenous nucleic acid molecules. The vector can comprise a virus or a recombinant virus; e.g., a baculovirus or recombinant baculovirus. The invention even further comprehends collecting expressed product, and/or virus or vector, e.g., baculovirus and/or the cells, as well as expressed product from the methods.

The invention therefore provides a method, for producing an expression product from a recombinant vector infected or transfected or inserted into a cell, or for producing a vector infected or transfected or inserted into a cell, comprising performing aforementioned or herein disclosed methods, wherein cells of the cell culture are infected or tranfected with or have inserted into them the recombinant vector, or the vector, either prior to or during the method. The recombinant vector can be a virus, e.g., a recombinant virus, such as a baculovirus and the cells can be cells susceptible to such a virus e.g., insect cells. The cells can be infected and/or transfected and/or have the vector inserted therein during the aforementioned and/or herein disclosed methods, e.g., during use and/or within inventive apparatus; and, collecting the cells or the expression product or the recombinant vector or the vector can be included.

Accordingly, the invention yet further comprehends uses of the expression products; e.g., as diagnostics, therapeutics, antigens, epitopes(s) of interest, vaccines, immunological compositions, therapeutic compositions, diagnostic compositions, etc.; and, the invention comprehends products from such uses, e.g., immunological and/or vaccine and/or diagnostic and/or therapeutic compositions comprising an antigen and/or epitope of interest and/or diagnostic protein and/or therapeutic wherein the antigen and/or epitope of interest and/or diagnostic protein and/or therapeutic is obtained from herein described methods and/or apparatus, and/or antibodies or antibody compositions elicited by such an antigen and/or epitope of interest (e.g., from administration of the antigen or epitope to a suitable animal), as well as methods involving such products, such as methods for inducing an immunological or immune response or protective immune response or therapeutic response comprising administering the composition comprising the antigen and/or the epitope of interest and/or the antibody and/or the therapeutic and methods involving diagnostic proteins from the invention, e.g., contacting a sample with a diagnostic protein obtained from this invention to ascertain the presence or absence of an antibody to the diagnostic protien.

The terms "comprises" and "comprising" can have the meaning given these terms in U.S. Patent Law; e.g., they can mean "includes" or "including".

Further embodiments of this invention will be set forth in the description that follows, and will become apparent to those skilled in the art and as learned by the practice of the invention.

BRIEF DESCRIPTION OF THE DRAWINGS

The following Detailed Description, given by way of example, and not intended to limit the invention to specific embodiments described, may be understood in conjunction with the accompanying Figures, incorporated herein by reference, in which:

FIG. 5 shows a graph describing Growth of Insect Cells in a High-Density Dialysis Bioreactor with In-Line oxygen Sparging;

FIG. 6 shows a bar graph comparing Yields of AcNPV Polyhedrin Protein in Standard and High-Density Cultures;

FIG. 7 shows a bar graph comparing Yields of Recombinant Hemagglutinin from Three Strains of Viral Influenza in Standard and High-Density Cultures;

FIG. 9 provides a Bioreactor diagram legend (legend of components; see FIGS. 1-4);

DETAILED DESCRIPTION

Figure 1:
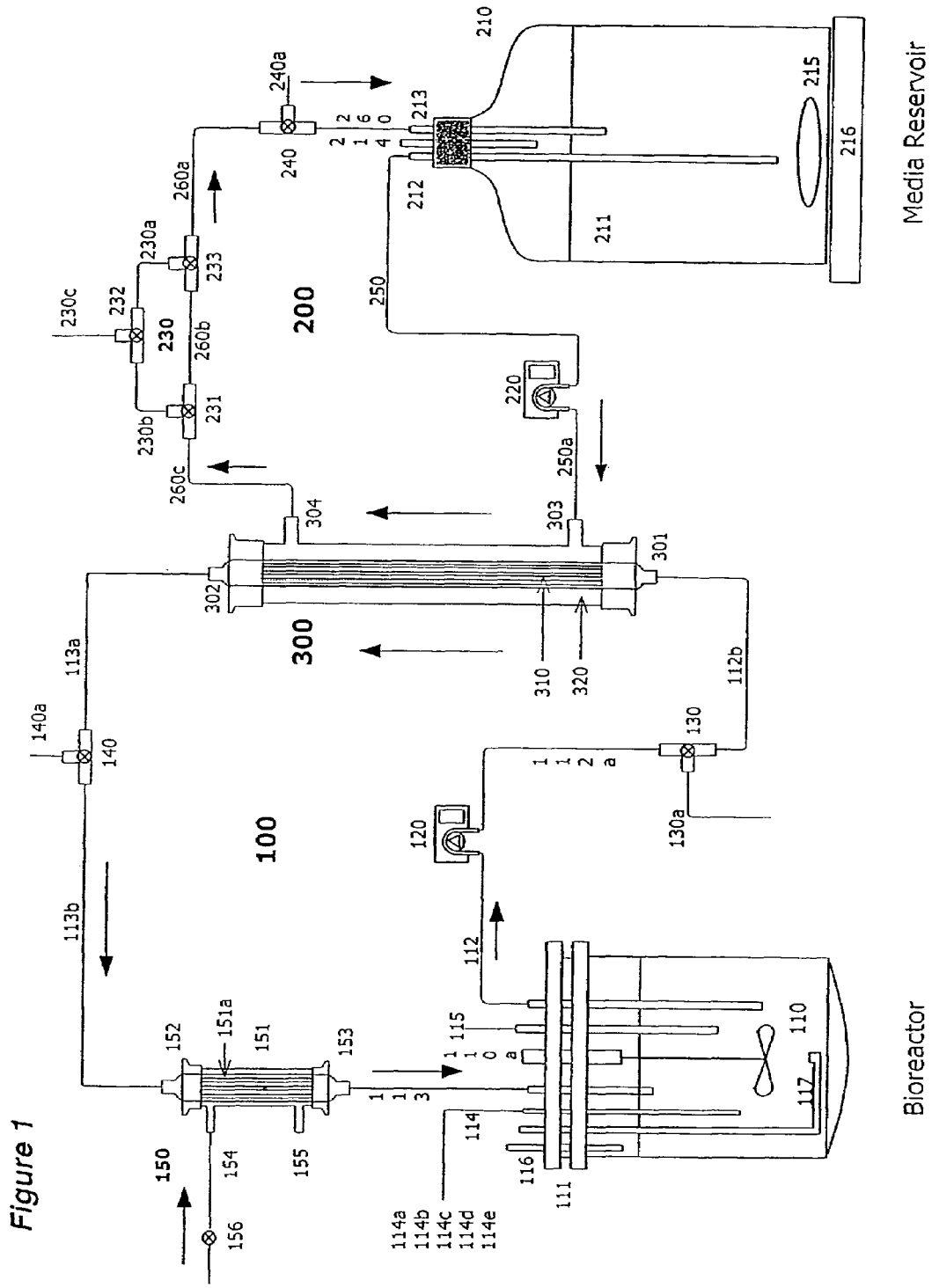
FIG. 1 shows a schematic illustration of a High-Density Dialysis Bioreactor with In-Line oxygenation.

A bioreactor/cell culture process desirably provides for at least one or more, and advantageously all of: rapid growth of cells, preferably to high density, nutrient utilization and waste removal, preferably efficient nutrient and/or waste removal, and optimum accumulation of biological substances of interest. "High density" can have the meaning given to this term in the art, e.g., literature, patents, such as those cited herein, and can mean cell densities as exemplified herein, and/or about ±15% or about ±10% about or ±5% or about ±3% or about ±1% of these values, but higher cell densities, e.g., higher than those reported herein and/or higher than about 10% or about 15% greater than values exemplified herein, are desirable. Advantageously, "normal" density can be a density achieved without the present invention, e.g., under standard conditions (such as stirred bioreactor with direct sparging into the bioreactor without circulation of cells or medium), and high density can be a 20% or 50% or 100% or 150% or 200% or even a 300%, 400% or 500% or more increase in cells over normal (note the Examples infra).

The apparatus and process of the present invention, while developed for and advantageously employed with respect to lepidopteran insect cells, provides beneficial conditions for many diverse cell types; namely, all cell types, including without limitation, eukaryotic and prokaryotic cells; vertebrate and invertebrate cells; animal and plant cells; fungus or yeast and bacteria cells; for instance, plant cells such as land plant cells and marine plant cells, monocot cells and dicot cells e.g. maize cells, tomato cells, tobacco cells; yeast cells such as *Saccharamyces cerevisiae* cells, *Saccharamyces pastorianus* cells *Pichia pastoris* cells; bacteria cells such as *E. coli, Bacillus* (e.g., *Lactobacilli*), *Staphylococci*; vertebrate cells such as fish cells (e.g., shark, salmon, rainbow trout, zebrafish, herring, mackerel cells), amphibian cells (e.g. frog, toad, salamander cells), bird or avian cells (e.g. chicken, turkey, duck, pigeon, dove cells), reptile cells (e.g. snake such as cobra), and mammalian cells (e.g., human, rabbit, hamster, mouse, rat, primate, cells such as VERO, HeLa cells, Chinese hamster ovary (CHO) cell lines, W138, BHK, COS-7, 293, MDCK, blood cells (e.g., red blood cells and white blood cells)); invertebrate cells such as land invertebrate cells, for instance, insect cells, e.g., lepidopteran cells such as *Spodoptera* (e.g., *Spodoptera frugiperda* such as Sf9 or Sf900+ or ATCC CRL 12579; see also U.S. Ser. No. 09/169, 178, filed Oct. 8, 1998), *Trichoplusia* (e.g., *Trichoplusia ni* such as cells as in Granados, U.S. Pat. Nos. 5,300,435, 5,298, 418), silkworm (*Bombyx mori*), dipteran such as mosquito (e.g. *Culicidae*) cells, fly cells (e.g. *Drosophila*), transformed insect cells (see, e.g., Ailor et al., "Modifying secretion and post-translational processing in insect cells," Current Opinion in Biotechnology 10:142-145 (1999); Pfeifer et al., "Expression of heterologous proteins in stable insect cell culture," Current Opinion in Biotechnology 9:518-21 (1998); McCarroll et al., "Stable insect cell cultures for recombinant protein production," Current Opinion in Biotechnology 8:590-94 (1997); U.S. Pat. No. 5,637,477), and marine invertebrate cells, for instance shrimp cells (including *Penaeus* such as *Penaeus monodon, P. japonicus* and *P. penicillatus*); e.g., typical cells that are used with eukaryotic replicable expression vectors such a *S. frugiperda* cells, VERO cells, MRC-5 cells, SCV-1 cells COS-1 cells, NIH3T3 cells, mouse L cells, HeLa cells, CHO cells, and the like. The cells can be recombinant; e.g., the cells can have been infected or transfected with or by a vector or otherwise have inserted therein a vector (e.g., before, during or after use of the cells in the bioreactor system and methods of use of the invention), and the vector can contain a particular nucleic acid molecule, e.g, a heterologous or exogenous nucleic acid molecule (as to either the cell or the vector or both); for instance, for reproduction and/or expression of certain nucleic acid (e.g., DNA) molecules.

It is advantageous in growing cells to supply and maintain nutrients and oxygen uniformly or substantially uniformly or with consistency or substantially consistently or regularly or substantially regularly, as well as maintain cell viability, whether in the cell growth or protein synthesis phase. Note for instance the regular variation in cell culture parameters in embodiments of the present invention, or the holding or of one or more parameters constant or uniform (or substantially constant or uniform).

Embodiments of the present invention demonstrate the applicability of the present invention to all cell types because addressing design issue with respect to insect cells provides teachings to practice the invention with respect to any cell type, since one can extrapolate from insect cells to other cells, and insect cells are a true test of the invention. For instance, insect cells require oxygen over and above what is required for most animal cells (Maiorella B, Inlow D, Shauger A, Harano D (1988) *Bio/Technology* 6: 1406). When infected by baculovirus, the oxygen requirement increases yet again (Kiouka N, Nienow A W, Emery A N, al-Rubeai M (1995) *Journal of Biotechnology* 38(3): 243). And, improper delivery of oxygen can result in cell damage and ultimately, cell death through shear forces related damage.

The invention provides many advantages. In at least certain embodiments, the invention is simple in that it can include three main components: A cell culture Loop 100. A Medium Replenishment Loop 200. And, Hollow Fiber Dialysis Device 300. Other embodiments can be simpler.

Further, components of the invention can be modular such that each module can be replaced during the culture process either as a planned event such as a requirement for optimal production of a biological substance, or as an unplanned event such as the failure of a component. This exchange of modules can occur without having to halt the culture process. The simplicity and modularity of the present invention make it flexible in that the invention can accommodate a variety of culture parameters such as cell type, and scale or process type such as batch or continuous.

Figure 10:
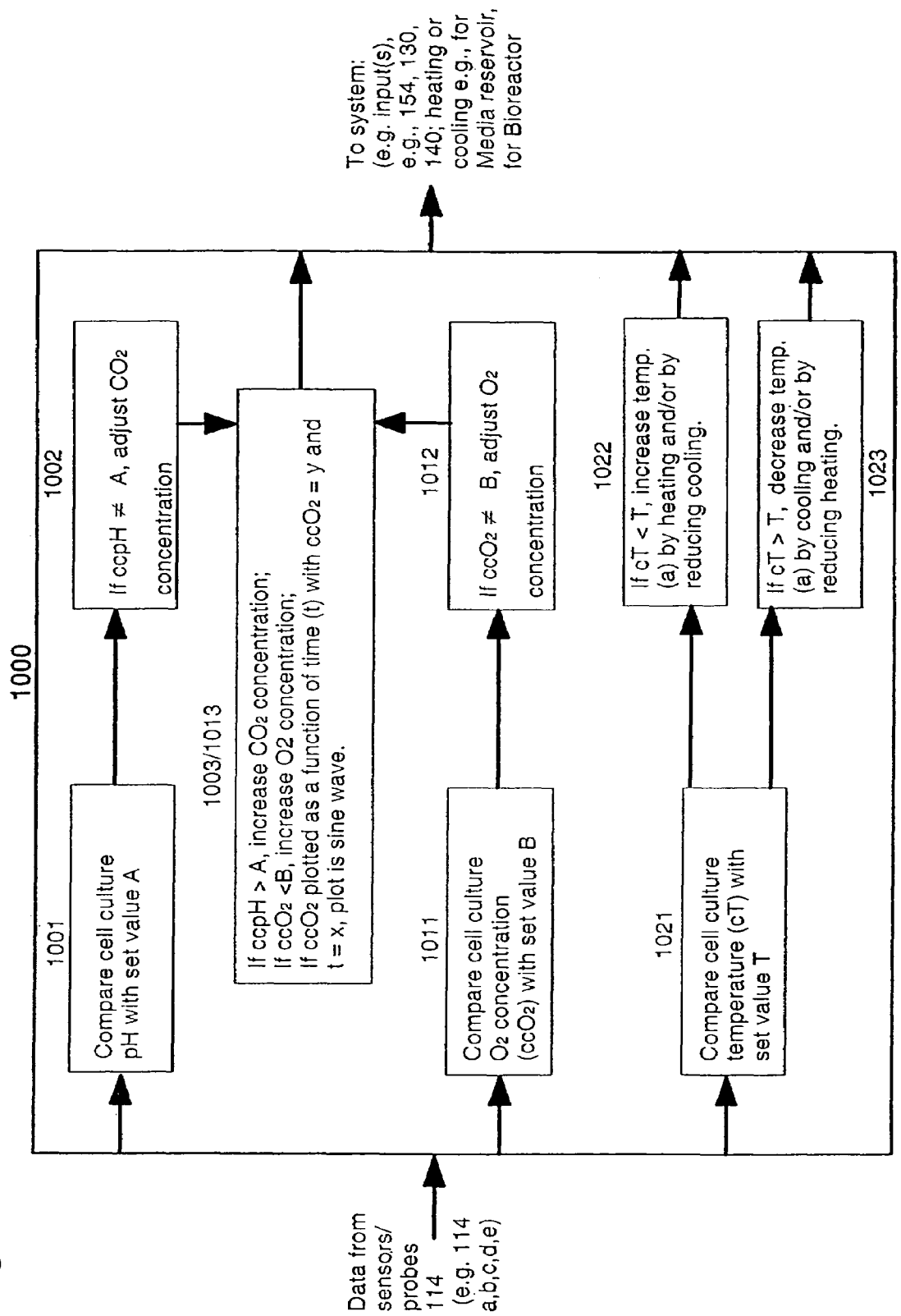
FIG. 10 shows a flow diagram with outputs from probes 114a-e going to microprocessor or processor or computer controlling parameters such as pH, carbon dioxide, oxygen, air, nitrogen, temperature and connected to system inputs therefor (e.g., 154, 130, 140; heating/cooling e.g., for media reservoir, for bioreactor) with pH, oxygen, carbon dioxide and temperature functions illustrated in the flow diagram; and, FIG. 11 shows CHO cell growth in a high density bioreactor according to the invention vs. growth in a control flask.

Further still, the simplicity, modularity and flexibility of the invention means that it lends itself to automation through the addition of appropriate sensors in the system; for instance as discussed herein, see, e.g., FIG. 10. These could monitor one or more or any combination or all of: temperature, pH, conductivity, dissolved oxygen, glucose level, cell density, carbon dioxide, and nitrogen, for example. A computer programmed with the optimum culture conditions can monitor the sensor data and adjust chemical or physical properties, such as pH (for instance by addition of carbon dioxide) or oxygen (for instance by addition of oxygen), or temperature, in response to sensor data. When deviations from the prescribed conditions are detected, the computer then automatically would adjust the appropriate culture parameters such as impeller speed, oxygen flow rate or medium flow rate until the culture conditions once again fall within acceptable ranges. Thus, this "feedback loop" between the sensor data and the computer would allow for unattended operation of the invention.

Advantageous embodiments can include means for dialysis. This means can be a hollow fiber filter; and, this has been found to be an important contribution to improving cell culturing system yields. These slightly flexible semi-permeable capillary tube devices are usually contained in a rigid encasement. Because they are semi-permeable, that is, they allow small molecular size material to pass through their pores while retaining the much larger intact cells, they are utilized in particularly advantageous embodiments to separate the desired biological product from the cells during fermentation. Another means for dialysis can be a tangential flow filter, i.e., another semi-permeable membrane useful as a dialysis means in this invention can be a tangential flow filter.

In certain advantageous embodiments, the dialysis means is present and an interface between the Cell Culturing Loop and the Medium Replenishment Loop. (See FIG. 1: Note that cell culture from bioreactor 110 flows through cell take-up and line 112 into line 112a (through action of pump 120), and passes through line 112b into the Hollow Fiber Dialysis Device 300 via Lumen input 301. Cell culture from Lumen input 301 flows into Lumen space 310 and out Lumen ouflow 302 to cell return line 113a. Lumen space 310 is within the hollow fiber filter of the hollow fiber filter device 300 (which has a cylindrical shape). From line 113a, cell culture flows into line 113b, and then passes though optional, but advantageously present, oxygenation loop 150 via lumen input 152 and lumen outflow 153 (at opposite ends of the lumen 151a of oxygenation loop 150), returning to bioreactor 110 via line and cell return 113. Media from media reservoir 210 flows through media take-up 212 into line 250 and to line 250a (through the action of pump 220) and into extra lumenal input 303 of the Hollow Fiber Dialysis Device 300. From extra lumenal input 303, media flows into extra lumen space 320, which has an exterior surrounding relationship to the hollow fiber filter of the Hollow Fiber Dialysis Device 300 and is within the lumen of the Device. The media then flows out extra lumenal outflow 304, through lines 260c, 260b, 260a and 260 back into media reservoir 210 via media return 213. Thus, media flows on the outside of the hollow fiber filter while cell culture flows through the interior of the hollow fiber filter, with dialysis occurring as the liquids pass on opposite sides of the filter—nutrients flowing from the media into the cell culture through the hollow fiber filter, waste from the cell culture flowing into the media through the hollow fiber filter (nutrients and waste products in the bioreactor and the dialysate are in equilibrium and do not necessitate continuous perfusion (dialysis used not only for removal of waste but also for addition of nutrients))—and the Hollow Fiber Dialysis Device is a dialysis means that is an interface between the Cell Culture Loop and the Medium Replenishment Loop.)

Having the dialysis means as an interface between the Cell Culturing Loop and the Medium Replenishment Loop provides advantages. For instance, in the practice of embodiments of the present invention, one can use a hollow fiber filter without: having to remove medium and the cells from the bioreactor vessel, then pass the medium and cells through the filtering device, with subsequent collection of the perfused fluid containing the desired biological substance and returning the medium with its cells to the original bioreactor vessel; or having to house cells of interest within the extra-lumenal space of the device itself, with perfused medium passing through the capillary tubes to the cells; or placing the unencased hollow fibers directly into the fermentation tank itself so that fresh medium can be more directly provided to immobilized or attached cells.

The inventive bioreactor system and methods of use can in certain advantageous embodiments involve a combination of improvements that together can provide for high-density growth and production of biologically important materials. In these embodiments, the design can provide favorable oxygen, and/or nutrient supplies and reduced shear forces necessary for high-density propagation of cells. These embodiments can include: continuous circulation of cells from the bioreactor, through a semi-permeable hollow fiber filter, then back to the bioreactor; in a manner that is analogous the circulation of the blood through the kidneys and also includes in-line oxygenation, as in the lungs; medium is pumped from a storage vessel to the hollow fiber filter and then circulates back to the storage vessel. In the hollow fiber filter, dialysis occurs between circulating replenishment media and cells; removing waste products and replenishing nutrients utilized to support the metabolism of the cells. The method in these embodiments compartmentalizes the process of culturing cells, and thereby producing important biological substances, into three discrete components: one containing the cells, one containing a volume of medium and the third a semi-permeable device allowing interaction between the cell compartment and the medium reservoir compartment. Thus, like circulating blood cells, cells in this bioreactor system can be maintained under conditions optimal for growth or production of cellular products.

Thus, the invention can involve a bioreactor for containing cell culture, dialysis means, and a media reservoir for containing media wherein the bioreactor is connected with the dialysis means and the media reservoir is connected with the dialysis means such that in operation there is dialysis between the cell culture and the media; and, each of the cell culture and media may be in circulation via circulation or pumping means.

Accordingly, in certain advantageous embodiments, the invention can further involve oxygenation means, illustrated in the Figures as an oxygenation loop within the cell culturing loop. The illustrated oxygenation means (see FIG. 1) includes oxygenator 151 that includes lumen 151a, gas input 154, gas output 155, lumen input 152 and lumen outflow 153 (with cell culture flowing from line 113b into lumen input 152 at the top of oxygenator 151 and out of the oxygenator at lumen outflow 153 at the bottom of oxygenator 151 and into bioreactor 110 via cell return 113). The gas input can, of course, be connected to an oxygen source, to provide oxygen to the cell culture; and, other gases can also be inputted through input 154, e.g., air and/or carbon dioxide and/or nitrogen. Furthermore, an alternative can be that input from line 113b flows into input 154 and output 155 is connected to line 113, with gas introduced at input 152 and exiting at outflow 153; i.e., the ports can be "flipped". Alternatively or additionally, oxygenation means can include introducing (e.g., at the point in FIG. 1 of the oxygenation loop) oxygen and/or an oxygen source or carrier into the cell culture (that diffuses oxygen into the cell culture), such as perfluorocarbon oxygen carriers, hemoglobin, and the like, either alone or in combination with one or more other gases and/or gas sources or carriers.

With respect to oxygen sources or carriers that can be used to diffuse oxygen into the cell culture, such as fluorocarbon or perfluorocarbon oxygen carriers or blood substitutes, mention is made of Flurovent, a liquid ventiliation, a flurocarbon liquid from Synthetic Blood International, Inc., that can replace or augment mechanical ventilation; Oxycite, an oxygen carrying perfluorocarbon from Synthetic Blood International, Inc., Oxygent, a perfluorocarbon oxygen carrier from Alliance Pharmaceuticals; see also L C Clark, Jr., F Gollan. Survival of mammals breathing organic liquids equilibrated with oxygen at atmospheric pressure. Science 152:1755-1756, 1966; T H Shaffer, M R Wolfson, L C Clark, Jr. Liquid Ventilation: State of the Art Review. Ped Pulmon 14:102-109, 1992; R E Hoffmann, H K Bhargava, S L Davis, L C Clark, Jr. Arterial blood gases and brain oxygen availability following infusion of intratracheal fluorocarbon neat liquids. Biomat, Art Cells & Immob Tech 20:1073-1083, 1992; L C Clark, Jr., R E Hoffmann, R B Spokane, P E Winston. Physiological evaluation of fluorocarbon emulsions with notes on F-decalin and pulmonary inflation in the rabbit. Mat Res Soc Symp Proc 110:129-134, 1989; LC Clark, Jr., RE Hoffmann, S L Davis. Response of the rabbit as a criterion of safety for fluorocarbon breathing and blood substitutes. Biomat, Art Cells & Immob Biotech 20:11085-1099, 1992; R J Kauftnan. Clinical development of perfluorocarbon-based emulsions as red blood substitutes. In "Blood Substitutes: Physiological Basis of Efficacy." Ed by Winslow et al, Birhauser, Boston, 1995; E Schutt, P Barber, T Fields, et al. Proposed mechanism of pulmonary gas trapping (PGT) following intravenous perfluorocarbon emulsion administration. Poster presented at the International Symposium on Blood Substitutes, San Diego, Mar. 16-20, 1993; V V Obraztsov, A S Kabalnov, K N Makarov, U Gross, W Radeck, S Rudigiger. On the interactions of perfluorocarbon emulsions with liver microsomal membranes. J Fluor Chem 63:101-111,1993; Riess, J. G. Overview of progress in the fluorocarbon approach to in vivo oxygen delivery. Biomater Artif Cells Immobilization Biotechnol. 1992; 20(2-4):183-202; Biro, G. P.; Blais, P. Perfluorocarbon blood substitutes. Crit Rev Oncol Hematol. 1987; 6(4):311-74; Navari, R. M.; Rosenblum, W. I.; Kontos, H. A.; Patterson Jr., J. L. Mass transfer properties of gases in fluorocarbons. Res. Exp. Med. 1977; 170: 169-180; Bowman, R. J. Red blood cell substitutes as artificial blood. Hum. Pathol. 1983 Mar. 14(3): 218-220; Lowe, K. C. Perfluorocarbons as oxygen-transport fluids. Comp. Biochem. Physiol. A. 1987; 87(4): 825-838; Rudowski, W. Modern oxygen carriers: state of art 1990. Mater. Med. Pol. 1990 January-March; 22(1): 3-7; Meinhert H., et al. On the perfluorocarbon emulsions of second generation. Biomater. Artif. Cells Immobilization Biotechnol. 1992; 20(1): 95-113; Tereshina, E. V., et al. Some aspects of perfluorochemical emulsion's interaction with blood. Biomater. Artif. Cells Immobilization Biotechnol. 1992; 20(2-4): 1001-1011; Riess, J. G., et al. Stabilization of Perflubron emulsions with egg yolk phospholipid. Biomater. Artif. Cells Immobilization Biotechnol. 1992; 20(2-4): 845-848; Lowe, K. C.; Armstrong, F. Biocompatibility studies with perfluorochemical oxygen carriers. Biomater. Artif. Cells Immobilization Biotechnol. 1992; 20(2-4): 993-999; Faithfull, N. S. Oxygen delivery from fluorocarbon emulsions—aspects of convective and diffusive transport. Biomater. Artif. Cells Immobilization Biotechnol. 1992; 20(2-4): 797-804; Lattes, A., et al. Microemulsions of perfluorinated and semi-fluorinated compounds. Artif. Cells Blood Substit. Immobil. Biotechnol. 1994; 22(4): 1007-1018; Spence, R. K., et al. Perfluorocarbons as blood substitutes: the early years. Experience with Flusol DA-20% in the 1980's. Artif. Cells Blood Substit. Immobil. Biotechnol. 1994; 22(4): 955-963; Spence, R. K. Perfluorocarbons in the twenty-first century: clinical applications as transfusion alternatives. Artif. Cells Blood Substit. Immobil. Biotechnol. 1995; 23(3): 367-380; Shah, N.; Mehra, A. Modeling of oxygen uptake in perfluorocarbon emulsions: some comparisons with uptake by blood. ASAIO Journal. 1996; 42: 181-189; Patel, S., et al. Modeling of oxygen transport in blood-perfluorocarbon emulsion mixtures. Part II: tissue oxygenation. ASAIO Journal. 1998; 44(3): 157-165; Hoffman, R., et al. Arterial blood gases and brain oxygen availability following infusion of intratracheal fluorocarbon neat liquids. Biomater. Artif. Cells Immobilization Biotechnol. 1992; 20(2-4): 1073-1083; Forman, M. B., et al. Role of perfluorochemical emulsions in the treatment of myocardial reperfusion injury. Am. Heart. J. 1992 November; 124(5): 1347-1357; Jacobs, H. C., et al. Perfluorocarbons in the treatment of respiratory distress syndrome. Semin. Perinatol. 1993 August; 17(4): 295-302; Holman, W. L., et al. Use of current generation perfluorocarbon emulsions in cardiac surgery. Artif. Cells Blood Substit. Immobil. Biotechnol. 1994; 22(4): 979-990; Wada, S., et al. Effects of FC43 emulsion against hyperacute rejection in rodent discordant xenotransplantation. J. Heart Lung Transplant. 1995; 14: 968-972; Tutuncu, A. S., et al. Evaluation of lung function after intratracheal perfluorocarbon administration in healthy animals. Crit. Care Med. 1996 February; 24(2): 274-279; Mosca, R. S., et al. Perfluorocarbon supplementation and postischemic cardiac function. Surgery. 1996 August; 120(2): 197-204; Sakas, D. E., et al. Perfluorocarbons: recent developments and implications for neurosurgery. J. Neurosurg. 1996 August; 85(2): 248-254; Ueno, T., et al. Efficacy of perfluorotributylamine/pluronic F-68 stememulsion (FC43se) against reperfusion injury in ischemic rabbit lungs. Transplant Proc. 1997 February-March; 29(1-2):1349-53; Clark, M. C., et al. Perfluorocarbons: future clinical possibilities. J. Invest. Surg. 1997 November-December; 10(6): 357-365; Goodnaugh L. T., et al. Oxygen carriers as blood substitutes. Past, present, and future. Clin. Orthop. 1998 December; (357): 89-100; Chiba, T., et al. Transabdominal oxygenation using perfluorocarbons. J. Pediatr. Surg. 1999 May; 34(5): 895-900; discussion 900-901.

The dialysis means in embodiments of the inventive bioreactor and methods of use is by itself believed to be novel. The oxygenator means in embodiments of the present invention, e.g., oxygen sparging and/or providing oxygen via an oxygenation loop containing a pore filter, is also by itself believed to be novel. Thus, embodiments of the invention can involve the dialysis means (or dialyzing) without necessarily also including the oxygenator means. Embodiments of the invention can involve oxygenator means (or oxygenating) without necessarily also including dialysis means. And, embodiments of the invention can include both dialysis means and oxygenator means (or dialyzing and oxygenating). (Indeed, dialyzing and oxygenating can be two steps or one step; for instance, if the media includes not only nutrients but also a source or carrier of oxygen such that at the dialysis means, nutrients and oxygen both pass to the cell culture and dialyzing and oxygenating can be performed in one step.)

Inventive bioreactor systems and methods of use can support the growth of cells, e.g. insect cells, to densities that are higher than those known to the inventors to have ever been reported. Inventive bioreactor systems and methods of use also produce virus, e.g., baculovirus and recombinant gene products in cells, e.g., insect cells, at very high cell densities. Furthermore, inventive bioreactor systems and methods of use can be employed at large scales and are suitable for the manufacture of recombinant DNA products in cultured cells.

Insect cells from *S. frugiperda* and other Lepidopteran insect species have been described in the literature and their general use to support the infection and replication of baculoviruses and recombinant baculoviruses or insect cell viruses and the production of recombinant proteins therefrom is well known (see, e.g., Smith et al., U.S. Pat. No. 4,745,051 (recombinant baculovirus); Richardson, C. D. (Editor), Methods in Molecular Biology 39, "Baculovirus Expression Protocols" Humana Press Inc. (1995)); Smith et al., "Production of Human Beta Interferon in Insect Cells Infected with a Baculovirus Expression Vector," Mol. Cell. Biol., 3(12): 2156-2165 (1983); Pennock et al., "Strong and Regulated Expression of *Escherichia coli* B-Galactosidase in Insect Cells with a Baculovirus vector," Mol. Cell. Biol., 4(3):399-406. (1984); EPA 0 370 573, U.S. application Ser. No. 920, 197, filed Oct. 16, 1986, EP Patent publication No. 265785; U.S. Pat. No. 5,911,982; and other documents cited herein).

In the baculovirus expression system, an inserted nucleic acid molecule, e.g., the foreign gene, the heterologous or exogenous nucleic acid molecule, for instance, DNA, is inserted into an insect virus vector, e.g., in a baculovirus vector, which is then used to infect cells of the inventive cell line, for expression of the DNA. The DNA preferably encodes an expression product. Similarly, when the inventive bioreactor process is used with the insect cell line infected with a recombinant baculovirus, at least one polypeptide of interest is produced.

Similarly, other vector systems for the expression of exogenous DNA are known; for instance, the poxvirus system; see, e.g., U.S. Pat. Nos. 4,603,112, 4,769,330, 5,174,993, 5,505,941, 5,338,683, 5,494,807, 4,722,848, WO 94/16716, WO 96/39491, Paoletti, "Applications of pox virus vectors to vaccination: An update," PNAS USA 93:11349-11353, October 1996, and Moss, "Genetically engineered poxviruses for recombinant gene expression, vaccination, and safety," PNAS USA 93:11341-11348, October 1996. In embodiments of the invention, instead of insect cells in the inventive bioreactor system and methods of use, one can use cells susceptible to expressing nucleic acid molecules of poxviruses—either heterologous or homologous nucleic acid molecules, e.g., cells susceptible to poxvirus infection and/or cells in which a poxvirus can have expression of at least some gene products (either heterologous or homologous gene products) without productive replication of the virus (e.g., wherein the cell is not naturally a host of the particular poxvirus such as infecting a mammalian cell with an avian poxvirus); and, these cells may be infected with a poxvirus or a recombinant poxvirus for reproduction of and/or expression from the poxvirus (or, one can use insect cells and infect them with an insect poxvirus or a recombinant insect poxvirus—either one that has reproduction and/or expression in such insect cells (e.g., wherein the insect cell is a natural host of the poxvirus) or has expression without productive replication in such insect cells (e.g., wherein the insect cell is not a natural host of the poxvirus)).

Similarly, there are other vector systems such as bacterial, and yeast systems, minichromoshomes, retrovirus vectors (e.g., murine leukemia viral vectors), retrotransposons or virus like particles, bovine papilloma virus vectors, SV40 based vectors, mammalian cell systems, other viral systems e.g. herpes virus systems, adenovirus systems, and DNA plasmid systems, inter alia; see, e.g., U.S. Pat. No. 4,769,331 (recombinant herpesvirus), Roizman, "The function of herpes simplex virus genes: A primer for genetic engineering of novel vectors," PNAS USA 93:11307-11312, October 1996, Frolov et al., "Alphavirus-based expression vectors: Strategies and applications," PNAS USA 93:11371-11377, October 1996, Kitson et al., J. Virol. 65, 3068-3075, 1991; U.S. Pat. Nos. 5,591,439, 5,552,143 (recombinant adenovirus), Grunhaus et al., 1992, "Adenovirus as cloning vectors," Seminars in Virology (Vol. 3) p. 237-52, 1993, WO 98/33510, Ballay et al. EMBO Journal, vol. 4, p. 3861-65, Graham, Tibtech 8, 85-87, April, 1990, Prevec et al., J. Gen Virol. 70,429-434, PCT WO91/11525; Ju et al., Diabetologia, 41:736-739, 1998 (lentiviral expression system); Felgner et al. (1994), J. Biol. Chem. 269, 2550-2561, Science, 259: 174549, 1993 and McClements et al., "Immunization with DNA vaccines encoding glycoprotein D or glycoprotein B, alone or in combination, induces protective immunity in animal models of herpes simplex virus-2 disease," PNAS USA 93:11414-11420, October 1996, and U.S. Pat. Nos. 5,591, 639, 5,589,466, and 5,580,859 relating to DNA expression vectors, inter alia., Fischbach et al. (Intracel) WO 90/01543 (method for the genetic expression of heterologous proteins by cells transfection); and Robinson et al., seminars in IMMUNOLOGY, vol. 9, pp. 271-283 (1997) (DNA vaccines). Cells useful with such other vector systems can be employed in the bioreactor system and methods of use thereof of the present invention; and, such cells can be infected or transfected or have plasmids containing exogenous DNA inserted therein, as the case may be depending on the cell and vector system, prior to or during or after growth and being employed in the inventive bioreactor and methods of use of the invention, e.g., for protein production using the inventive bioreactor and methos of use via those cells and another vector system.

With respect to terms, reference is made to documents cited herein, and generally to Kendrew, The Encyclopedia Of Molecular Biology, Blackwell Science Ltd., 1995 and Sambrook, Fritsch and Maniatis, Molecular Cloning, A Laboratory Manual, 2nd Ed., Cold Spring Harbor Laboratory Press, 1982 ("Maniatis et al., 1982").

CERTAIN SYSTEMS OF THE INVENTION: Systems and certain advantageous embodiments of the invention can be practiced is illustrated in FIGS. 1 to 4, 9 and 10.

Figure 2:
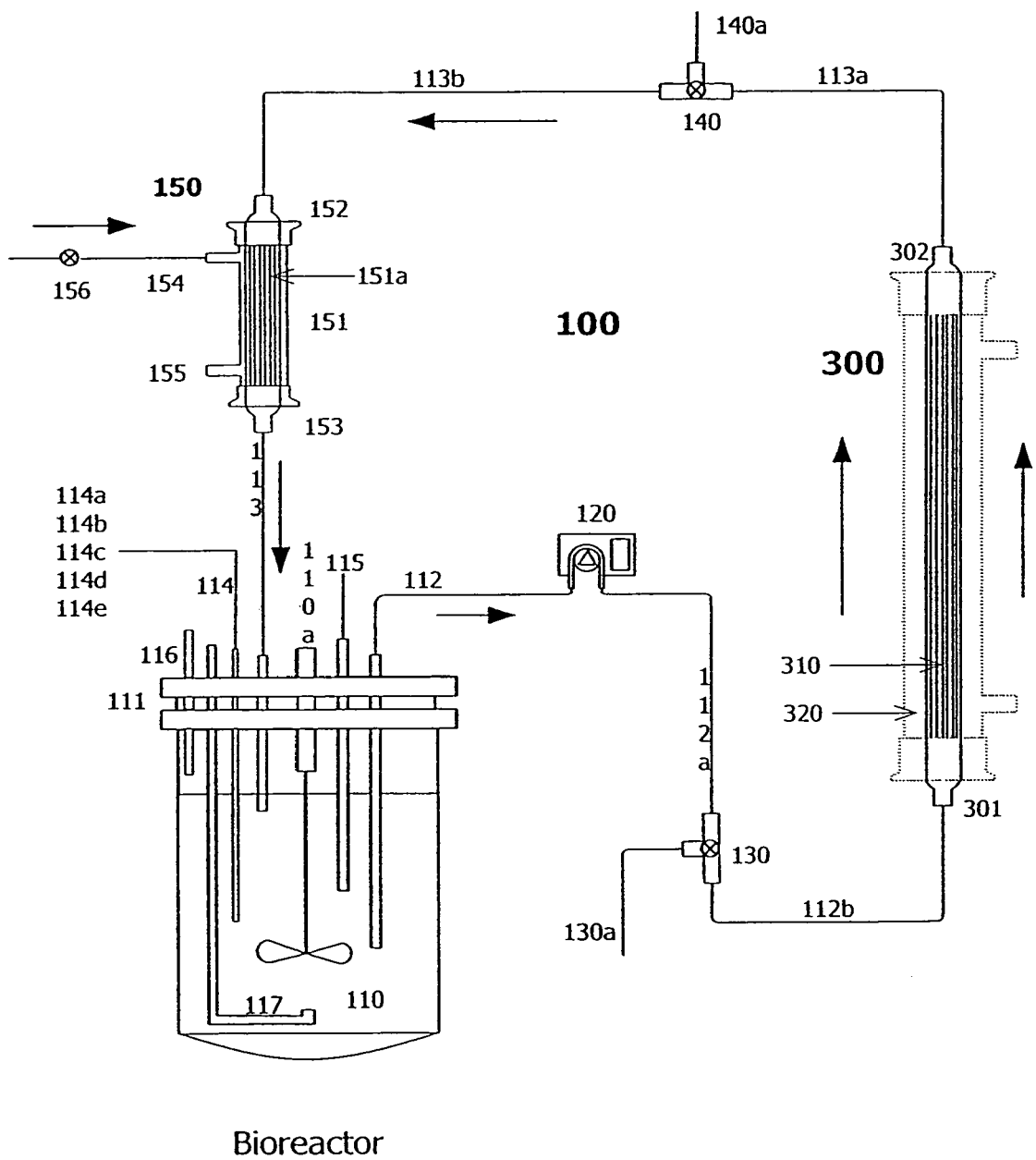
FIG. 2 shows a schematic illustration of the cell culturing loop of FIG. 1.
Figure 3:
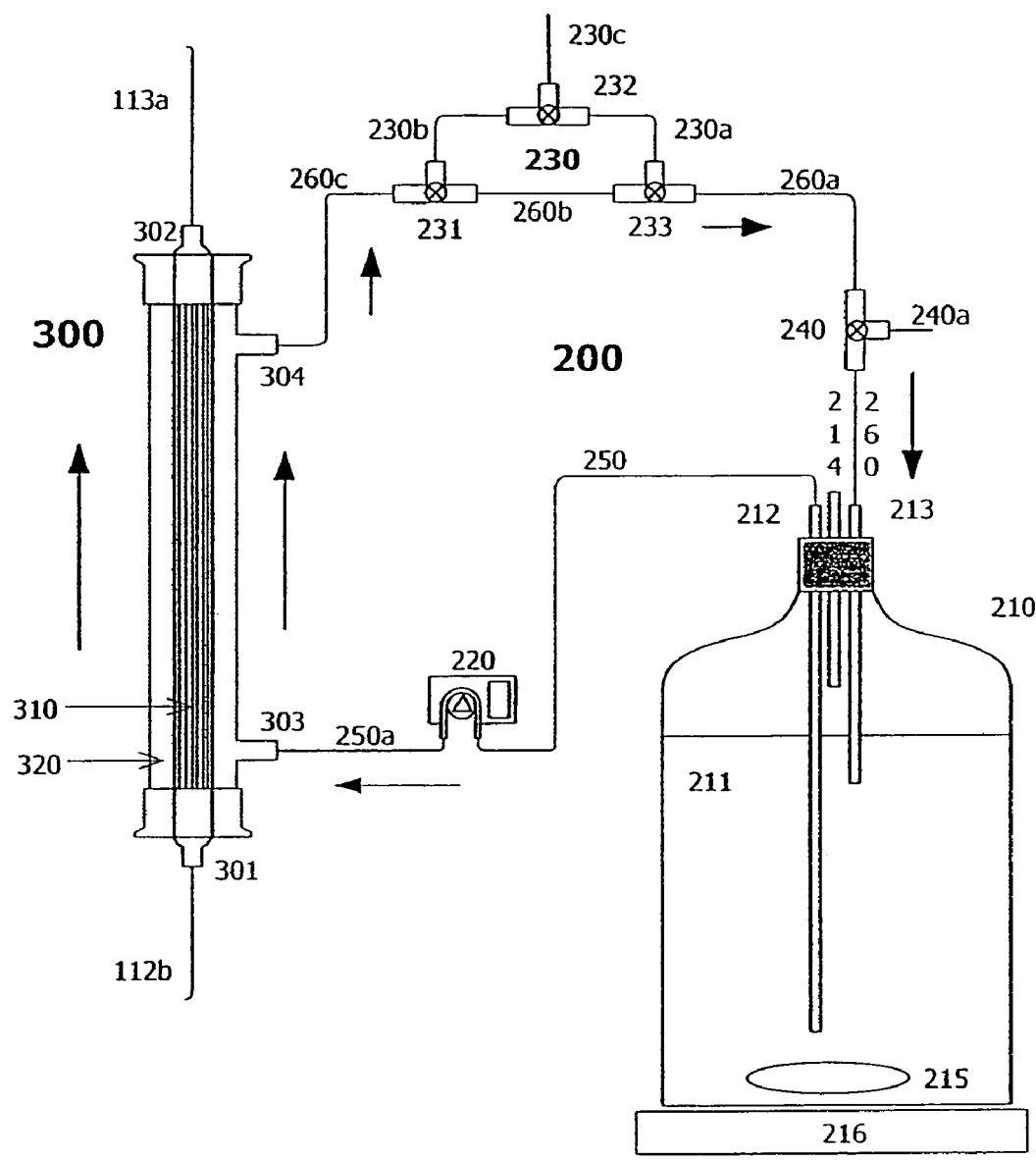
FIG. 3 shows a schematic illustration of the medium replenishment loop of FIG. 1.
Figure 4:
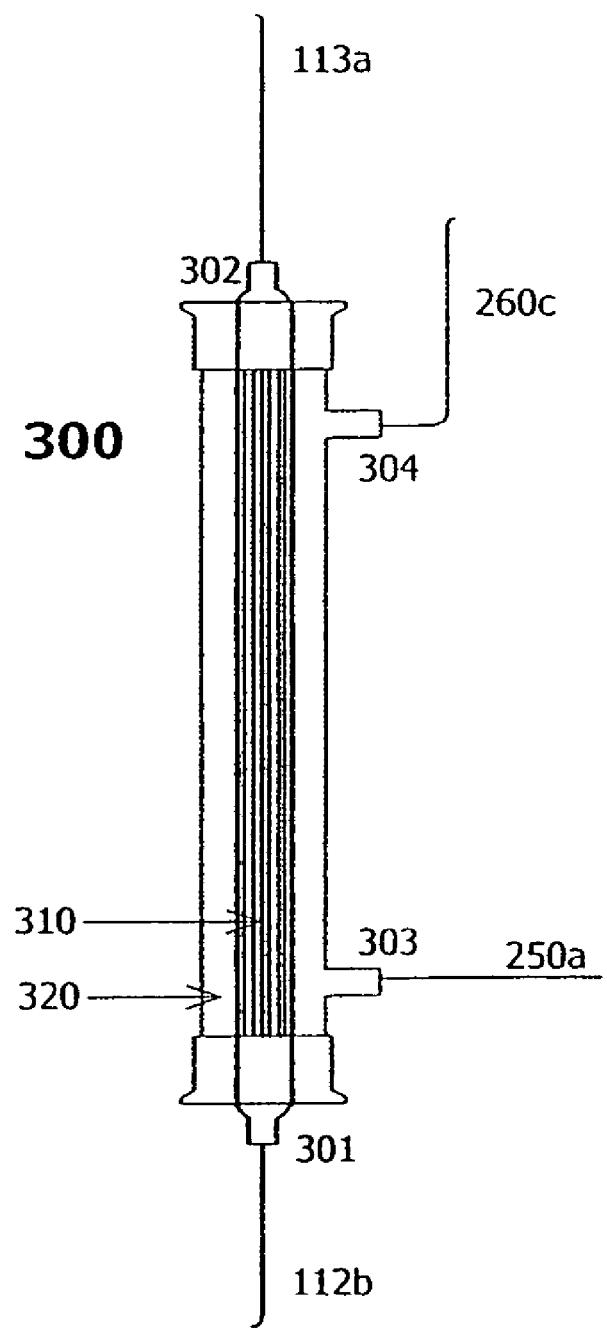
FIG. 4 shows a schematic illustration of the hollow fiber dialysis device of FIG. 1.

As shown in FIG. 1, a system can include three interconnected modules, the cell culturing loop 100, the medium replenishment loop 200 and the hollow fiber dialysis device 300. FIGS. 2-4 show these loops and device, with FIG. 9 listing components in certain advantageous embodiments of the invention, and FIG. 10 providing a flow diagram of the processor, microporcessor or computer functions in an embodiment of the invention.

THE CELL CULTURING LOOP: The cell culturing loop 100 can include a bioreactor 110 (that contains cell culture or culture in use), advantageously a stirred tank bioreactor, onto which is attached a headplate assembly 111. This headplate can contain a number of ports 112-115 through which the contents of the bioreactor 100 can be circulated, sampled and monitored. Thus, the bioreactor 110 can include optional stirring means, illustrated in FIG. 1 by mechanical stirrer 110a that has its motor positioned above bioreactor 110; but, other stirring means can be employed, such as a magnetic stirrer (as in the media reservoir; however, the stirrer should not interfere with probes or other devices that may be present and may monitor or control parameters within the cell culture and a magnetic stirrer may so interfere as a magnetic field in motion can generate an electrical field and such fields could interfere).

In a preferred embodiment, the ports can include a cell take up port 112 through which cells in culture are removed from the bioreactor using a pump 120, and a cell return port 113 through which the cells are returned to the bioreactor 110 following circulation, e.g., through the hollow fiber dialysis device 300, the optional at least one or a number of probe ports 114 to measure and/or control culture conditions (e.g., probe ports 114a to 114e—more or less probe ports can be provided, depending upon how many conditions one wishes to monitor or have controlled e.g. monitor and/or control via a processor, computer or microproscessor; for instance, there can be a probe for any one, or any combination, or all of: pH, conductivity, oxygen, carbon dioxide, nitrogen, glucose (and/or other nutrient(s)), ammonia (and/or other waste product(s)), temperature, cell density, cell count; and, these probe(s) can lead to one or more microprocessor, processor or computer, which in turn can be connected to sources for supplying or altering any one or all of these parameters, whereby the parameters are altered or supplied in response to measurements from the probes), the optional at least one sampling port 115 through which culture aliquots can be removed e.g., sterilely removed, to microscopically examine the culture or to directly measure culture metabolites for example, and a vent tube 116 that allows for pressure equilization in the bioreactor 110.

The cell culturing loop 100 can also optionally include at least one three-way valve, illustrated as two three-way valves 130 and 140, through which culture components can either be sterilely added or removed (e.g., via lines 130a or 140a) without having to access the bioreactor directly. Note that addition or removal of culture components can occur at either three-way valve. Further, note that these three-way valves can be controlled by a processor, microprocessor or computer; for instance, they can be opened and shut for introduction or removal of components automatically, e.g., opened automatically for introduction of components in response to data collected at the sensors/probes 114.

Additionally, illustrated embodiments have the cell culturing loop 100 also including the optional oxygenation loop 150 that allows for in-line addition of oxygen and/or other gases to the culture. This oxygenation loop contains an oxygenation device 151 that in the preferred embodiment is a hollow fiber oxygenator. In this oxygenator would be a lumen inflow port 152 through which the circulating cell culture would enter the lumen of the oxygenator, a lumen outflow 153 through which the circulating cell culture would exit the oxygenator, a gas input port 154 through which oxygen or a gas mixture containing oxygen would enter the oxygenator, a gas output port 155 through which excess gas would leave the oxygenator and a selenoid 156 that would control the amount of oxygen added. Note that the placement of the oxygenation loop is, in a preferred embodiment, such that oxygen is added after culture medium dialysis in the hollow fiber dialysis device 300 but before the circulating culture medium is returned to the bioreactor 110. Note further that the input at gas input 154 can be automoated, e.g., controlled by a processor, microprocessor, computer or the like, such that gas input 154 can be used for introduction of oxygen and other gases such as nitrogen, air, and carbon dioxide; for instance, in response to data from probes/sensors 114. Thus, data from probes/sensors 114 can go to a microprocessor, processor or computer, that adjusts gas input at gas input 154 in response to that data. And, as mentioned, oxygenation means other than the oxygenation device 151 can be employed in the practice of the invention. And, note that as discussed herein, the ports of oxygenation device 151 can be "flipped"; e.g., line 113b can flow into input 154 and output 155 can flow to line 113, with gas introduced at port 152 and exiting at outflow 153.

THE MEDIUM REPLENISHMENT LOOP: The medium replenishment loop can include media reservoir 210, a pump (or pumping means or circulating means) 220, an optional valve loop 230 and an optional individual valve 240.

The media reservoir 210 can include closed media vessel 211 (that contains media in use) take up line 212 that allows for the media to be circulated from the vessel 211, a vent tube 214 that allows for pressure equalization in the media vessel, and optionally stirring means such as stir bar 215 that agitates the media in the vessel 211. The stir bar 215 movement can be powered by a variable speed magnetic motor 216 onto which the media vessel 211 is placed; or, there can be other stirring means provided, such as a mechanical stirrer that is powered by a motor above the media reservoir (cf stirrer 110a).

The media is circulated from the vessel 211 by pump 220 to the hollow fiber dialysis device 300 (extra-lumenal input 303) via a media outflow lines 250 and 250a (that are on either side of the pump). After passing through the Hollow Fiber Dialysis Device 300, the media exits the Device via extra-lumenal outflow 304. From outflow 304, media passes through lines 260c, 260b, 260a and 260 to media return tube 213, through which media returns to the media vessel 211 (after it has been through the hollow fiber dialysis device 300).

The media return path can include optional extraction loop 230 that can include one or more and preferably three, three-way valves 231,232 and 233. The first three-way valve 231 can be used to divert the flow of return media to optional line 230b to the optional second three-way valve 232 that can be used to collect (e.g., sample) media after it has passed through the hollow fiber dialysis device 300 to analyze the media for culture metabolites in an in-line fashion. In its default position the first three-way valve 231 bypasses the extraction loop 230. The third three-way valve 233 serves to direct the media flow back to the main return lines 260a, 260 and 213 (from valve 232 and line 230a), or in its default position completes the bypass of the extraction loop 230 by the media. Another item in the medium replenishment loop is the optional sampling three-way valve 240 between lines 260a and 260 (downstream of the extraction loop, between the extraction loop and the media reservoir) where, for instance, additional media can be obtained for analysis (via line 240a). The default position of this valve 240 simply returns the media to the media vessel 211.

Alternatively or additionally, the extraction loop and/or the valve 240 can run to or be supplied with (e.g., via line 240a) a series of sensors or probes (e.g., glucose, nutrient content, and/or ammonia, waste content, etc.); and, these probes or sensors can be connected to a processor or computer or microprocessor that can collect information and/or be further connected to supply lines for the media or components thereof.

For instance, media can come out of line 230c, be run through yet another dialysis loop, e.g., to remove waste etc. and increase nutrient concentration and then return to the medium replenishment loop via valve 240. Consider that at predetermined times, valves 231 and 230 can be automatically opened by a processor, microprocessor or computer, for sampling parameters of the media, e.g., glucose, nutrients, pH, conductivity, etc. and that in response to that data, media can be run through line 230c to a dialysis loop (not shown) for removal of waste and increase of nutrient concentration and then return to the medium replenishment loop via valve 240.

Alternatively or additionally, sensors, probes, etc. at line 230c can sense glucose/nutrient concentration and/or ammonia/waste concentration and/or pH and/or conductivity etc., and additional glucose/nutrients and/or liquid to dilute the media and/or components of the media can be added via valve 240 and line 240a, to adjust glucose/nutrient concentration and/or ammonia/waste concentration and/or pH and/or conductivity etc., in response to the measurements taken at line 230c; and, this can all be done via a processor, microprocessor or computer connected to the sensors/probes at line 230c and the supply line(s) 240a feeding into valve 240. (Indeed, valves 231, 232, 233 and 240, as well as all valves in the operation of the invention, can be automatically controlled, e.g., controlled by way of a processor, microprocessor, computer, etc.; e.g., at a predetermined time the processor, microprocessor, computer causes valves 231 and 232 to open to allow a sample of media to run from valve 231 to line 230b and then to valve 232 and out line 230c to sensors/probes, for a data sampling, with those valves subsequently closed for normal operation; and, valve 240 would be automatically opened for introduction of any necessary components via line 240a to adjust the media in response to the readings from the sensors/probes.)

Thus, a microprocessor, processor or computer could first ask if the time is such for a sampling of the media, and if yes, then appropriately open valves 231 and 230 for the sampling. The processor can then collect data regarding pH and/or glucose/nutrient concentration and/or ammonia/waste concentration and/or conductivity, etc. and if the data values are not in accordance with preset optimum values, then either direct the media through another dialysis loop and send the further dialyzed media back to the reservoir via line 240a and valve 240 or add appropriate components to the media via line 240a and valve 240.

THE HOLLOW FIBER DIALYSIS DEVICE: The hollow fiber dialysis device is composed of a lumen space 310 and an extra-lumenal space 320. In a preferred embodiment, material from the cell culturing loop 100 is pumped through the lumen space 310 and media from the media replenishment loop 200 is pumped through the extra-lumen space 320.

CERTAIN PROCESSOR/MICROPROCESSOR/COMPUTER FUNCTIONS: FIG. 10 provides a flow chart of certain functions that can be automated in the practice of certain embodiments of the invention.

Data from probe/sensor 114 or 114$a$-$e$, such as any one of or any combination of or all of pH, oxygen concentration, carbon dioxide concentration, nitrogen concentration, temperature, conductivity, glucose/nutrient level ammonia/waste level, is fed to processor, microprocessor or computer 1000 that can advantageously be a BioFlo3000 or equivalent commercial product; and, the processor, microprocessor or computer is connected to sources for ingredients and inputs of the system such that the processor, microprocessor or computer can add ingredients to the system via inputs in response to data from the sensors/probes.

In step 1001 there is a comparison between the cell culture pH (ccpH) with a set value "A". "A" can be a pH in the range of about 6 to about 7.4, for instance, about 6 to about 7, such as about 6.1 to about 6.7, e.g., about 6.1 to about 6.5, and advantageously about 6.1 to about 6.35 such as about 6.25 (an optimal value for certain insect cells employed in exemplified embodiments). "A" can be set to a pH that is optimal for the particular cells employed in the inventive bioreactor system and methods of use thereof. In step 1002 the processor, microprocessor or computer asks if ccpH does not equal the set value "A" and if so, directs towards adjusting carbon dioxide concentration in the system; that is carbon dioxide is employed to control pH and the trigger is the set value "A", e.g., about 6.25.

In step 1011 there is a comparison between the cell culture oxygen concentration ($ccO_2$) with a set value "B". "B" can be in the range of about 30% to about 90% such as about 40% to about 80%, for instance about 50% to about 70%, advantageously about 60% (optimal values for certain insect cells employed in exemplified embodiments). Thus, "B" can be greater than 40%, e.g., greater than 40% and can go as high as about 90% or even 95%; an advance in the art. "B" can be set to an oxygen concentration that is optimal for the particular cells employed in the inventive bioreactor system and methods of use thereof (for instance, less oxygen if the cells tend to optimally perform under more anaerobic conditions, and the like). In step 1012 the processor, microprocessor or computer asks if $ccO_2$ does not equal the set value "B" and if so, directs towards adjusting oxygen concentration in the system.

Steps 1002 and 1012 flow to step 1003/1013. Step 1003/1013 directs the system as follows: If ccpH>A (e.g., if pH rises above trigger value such as 6.25), then increase carbon dioxide concentration (e.g., add carbon dioxide at input 154); if $ccO_2$<B, then increase oxygen concentration (e.g., add oxygen at input 154); and, $ccO_2$ can vary as a function of time t; e.g., if $ccO_2$ plotted as a function of time t, with $ccO_2$=y and t=x, plot can be a sin wave (for instance, the x axis runs through the y axis at point B, e.g., oxygen concentration of approximately 60%, with the amplitude being approximately 20% to 30%, e.g., the high point of the wave above the x axis can be at about 80% to 90% and the low point of the wave below the x axis can be at approximately 40% to 30%, with the oxygen concentration cycling from approximately 80 to 90% to approximately 40 to 30% over a time of about 10 to about 30 minutes, advantageously about 20 minutes, e.g., there can be two waves—one above the x axis and one below the y axis—about every 10 to 30 minutes advantageously about every 20 minutes, such that if "frequency" in this instance is the number of waves that pass a point about 10 to about 30 minutes, advantageously about 20 minutes, then the frequency is 2, or there is a wavelength about 10 to about 30 minutes, advantageously about 20 minutes).

Thus, carbon dioxide can be used to control pH, with the trigger being the set value for the pH, e.g., about 6.25; and, if the pH rises above this value, the carbon dioxide is "turned on"—added to the system. The addition of carbon dioxide, of course, reduces the oxygen concentration, and the system allows the oxygen concentration to fluctuate a relatively constant amount above and below the set value, or cycle over time (e.g., about 10-30 min. such as about 20 min), for instance, from about 30 to about 90% or about 40 to about 80%, with about 60% being a set value (i.e., about 20-30% above 60% and about 20-30% below 60& over a course of about 10-30 min such as about 20 min). The carbon dioxide thus can be set to 0 to 100%, as it is a variable that is adjusted by the microprocessor, processor or computer; in contrast to any previous reports advising that carbon dioxide accumulation is a problem. Further, the apparatus and methods of the invention are surprising, especially as insect cell cultures reportedly do not require $HCO_3^-/CO_2$ buffering (Karmen et al., supra).

This sin wave or cycling or rhythm or periodicity that has been observed when the system is automated can be a function of mechanical or chemical or biological processes occurring within the system. However, but without wishing to necessarily be bound by any one particular theory, it is believed that pH changes can occur due to cellular activites, e.g., ammonia and lactic acid can be released as wastes from cells, with a change in pH. pH change can trigger the addition of carbon dioxide. The addition of carbon dioxide can cause a lowering of the oxygen concentration. And lowering of the oxygen concentration can cause an addition of oxygen to the system (or a decrease in the addition of other gases to the system). That is, there can be a cycling of the oxygen via carbon dioxide adjustments based on pH. The nature of the cycling (e.g., sin wave vs. another wave such as cosine, amplitude and frequency of wave, etc.) can be adjusted by varying the set values e.g., for instance the values for oxygen, and/or pH.

In step 1021 there is a comparison between the temperature of the cell culture, cT, with a set value for temperature, T. At step 1022, the question is whether cT<T, and if so, then the microprocessor, processor or computer directs increasing temperature or heat applied and/or reducing cooling. At step 1023, the question is whether cT>T, and if so, then the microprocessor, processor or computer directs decreasing temperature or heat applied and/or increasing cooling (a heating/cooling jacket can be supplied in a surrounding relationship to the bioreactor and/or the media reservoir). T can be set to a value that is optimal for the cells, for instance, depending upon whether the cells function at low temperatures or high temperatures, such as about 15° to about 55° C., such as about 20° to about 40° or 35° C., advantageously about 25° to about 35° C., for example about 26° to about 30° C. or about 20° to about 28° C. such as about 24° C. to about 28° C.; and in exemplified embodiments about 28° C. (but, like other parameters, e.g., pH, oxygen, etc. temperature is set to a value that is optimal to the particular cell employed in the system).

Thus, as illustrated in FIG. 10, the output from microprocessor, processor or computer 1000 is to the system, e.g., inputs such as 154, 130$a$, 140$a$ and heating/cooling for the media reservoir or for the bioreactor. Accordingly, in an embodiment of the invention data from sensors/probes 114 can be sent to microprocessor, processor or computer 1000 that adjusts and/or controls pH, oxygen, temperature and carbon dioxide, with set values for these parameters; and, gas input into the system is oxygen, carbon dioxide, nitrogen and air. In practice of the invention, gases from Tech-Air manufactured by BOC Air Co. are advantageously employed.

Accordingly, in an embodiment of the invention there can be sensors/probes and/or controls for oxygen, carbon dioxide, temperature and pH; or for oxygen, carbon dioxide and pH (e.g., steps 1021, 1022 and 1023 can be omitted by the microprocessor, processor or computer; for instance, system run at room temperature, such as a room maintained at a fairly constant temperature).

In further embodiments, nitrogen can be set and adjusted as is optimal for the cells. Air can be added as is optimal for the cells or in response to oxygen and carbon dioxide levels. Further still, glucose and/or nutrient levels and/or ammonia and/or waste levels and/or conductivity can be measured via sensors/probes 114, with the microprocessor, processor or computer adding glucose, nutrients, etc. at any or all of inputs 130a, 140a and 240a; that is, the microprocessor, processor or computer can add to either or both loops of the system.

STILL FURTHER EMBODIMENTS: As mentioned, the use of the dialysis device is considered novel. Thus, a variation on the present invention can be wherein oxygenation loop 150 of FIG. 1 is omitted (such that line 113b runs directly into cell return 113). Oxygenation can be omitted in these embodiments or supplied by alternative means such as by chemical means added to the system.

Also as mentioned, use of the oxygenation loop 150 is considered novel. Accordingly, a variation on the present invention can be wherein hollow fiber dialysis device 300 is omitted (such that line 112b connects to line 260c and line 250a connects with line 113a). In these embodiments, waste removal can be performed at the end of cell growth or by alternative means.

The invention can be used for producing important biological substances including recombinant proteins, viruses and the cells themselves. The invention in advantageous embodiments can provide a cell culture unit, a bioreactor; the replenishment medium unit, a reservoir of nutrient medium; a semi-permeable membrane unit, the hollow fiber filter; and an oxygenation unit, an external source of oxygen and/or other gases.

The invention is advantageously applicable to growing cells such as insect cells, and generating vectors such as viruses, e.g. baculovirus, for instance, recombinant vectors such as recombinant viruses, e.g., recombinant baculovirus, and to expression of recombinant proteins therefrom.

The generation and use of recombinant vectors such as viruses, e.g., baculovirus, is known; for instance, from documents cited herein, including the patent applications and patents cited herein and documents cited in those patent applications and patents. The conditions limiting the growth of cells such as insect cells are nutrients, oxygen, and the levels of growth factors and inhibitors. The nutrient requirements for cells such as insect cells have been studied extensively and a variety of highly enriched commercial culture media, including serum-free media, have been developed. After nearly 20 years of research into these improved media formulations, prior to the present invention, there have been no significant improvements have been made on the growth rates, density, or expression levels of cells such as insect cells e.g., S. frugiperda and other lepidopteran insect cells; with only minor improvements in the yield of vectors such as viruses, e.g., baculoviruses or vector or virus, e.g., baculovirus gene products.

The S. frugiperda Sf-900+ (also termed herein Sf-900) cell growth is exponential at concentrations as low as $0.5\times10^6$ cells/mL up to $6\text{-}9\times10^6$ cell/mL. Interestingly, the cessation of the growth of insect cells occurs when the medium is still nutritionally sufficient suggesting that other factors, such as high levels of cell growth factors or other factors, may inhibit cell growth. Even more dramatic is the observation that infection of Sf-900+ cells with baculoviruses is inhibited at cell densities of $3\times10^6$ or higher suggesting again that there are inhibitory factors in the media. Also, the oxygen demand increases following infection reaching a peak about 2 days post infection of approximately twice the oxygen required during cell growth.

Especially advantageous elements of an improved bioreactor system and process for the growth of S. frugiperda cells and the production of recombinant protein are found in FIGS. 1-4 and 9, and optionally also in FIG. 10: High-Density Dialysis Bioreactor with In-Line oxygen. FIG. 2, shows a stirred cell bioreactor 110 with an outside loop for the circulation of cells from the bioreactor to a semi-permeable membrane, preferably a hollow fiber filter 300. The cell suspension circulates through the filter, preferably the internal partition (lumen) 310 of a hollow fiber filter, then back to the bioreactor; labeled the Cell Circulation Loop in the drawing. Also provided, as shown in FIG. 3, is a vessel 210, also with an outside loop for the circulation of medium through a semi-permeable membrane 300, preferably a hollow fiber filter. The medium (called the regeneration medium or media) circulates through the filter, preferably the external partition (extra-lumenal) 320 of a hollow fiber filter; called the Media Circulation Loop. The filter is advantageously semi-permeable, e.g. with pores of up to about 0.60 to about 0.70, such as about 0.65 µM, in diameter, which excludes cells from passing from the bioreactor to the regeneration medium but allows smaller molecules like glucose and amino acids or waste products like lactic acid and ammonia to diffuse across the membrane. (The pore size can vary depending upon the cells employed in the bioreactor system and process of the invention, e.g., smaller pore size for smaller cells.)

The hollow fiber filter (FIG. 3) in this bioreactor system and process acts much like blood vessels in an animal where blood circulating through the gastro-intestinal tract acquires recently absorbed nutrients and passing through organs like the liver and kidneys where additional nutrients and metabolic waste products, respectively are added or removed from circulating blood.

In a preferred embodiment, a second hollow fiber device 150 optimized for the exchange of oxygen gas is inserted prior to the cell return port of the bioreactor. It is preferred that oxygen is added to the cell circulation loop immediately prior to return as this configuration reduces the lag time between the disolved oxygen sensor located internally in the bioreactor and return of oxygenated cells into the bioreactor. This minimizes the possibility of over oxygenating the system.

Or, in yet a further alternative embodiment, a second hollow fiber device, optimized for the exchange of oxygen gas, is prior to or after the hollow fiber filter device employed for medium replenishment.

Or, in another alternative embodiment, in-line oxygen is added directly through a valve (e.g., a Y or T valve) in the cell circulation loop immediately before the hollow fiber filter (such that the hollow fiber filter is functioning for dialysis between the media and the cell culture and to dissolve oxygen into the system, e.g., oxygen is mixed with circulating cells and media, as it passes through the lumen of the hollow fibers in the filter device and is carried back to the bioreactor as exceedingly small bubbles or dissolved in the culture medium).

Any excess gas diffuses into the bioreactor tank head space and out a vent in the head plate of the bioreactor.

The circulating flow of cells in the cell circulation loop and the flow of regenerating medium in the media circulation loop are advantageously controlled with pumping or circulating means and these can be peristaltic pumps. The two streams can flow either in concurrent directions or in counter-current directions with equal success. The pumps can also be controlled by the processor, microprocessor or computer, e.g., to adjust flow rate in response to temperature, pressure, or other parameters such as pH, conductivity, amount of glucose/nutrient or ammonia/waste in system, carbon dioxide, or oxygen.

In certain embodiments described and exemplified herein, the bioreactor is a stirred two liter tank bioreactor (but, the invention is not limited to this size bioreactor), S. frugiperda insect cells such as Sf-900 (also termed herein Sf-900+) are seeded in two liters of cell medium. The temperature of the cells is maintained at about 20° C. to about 28° C. such as about 24° C. to about 28 C, e.g., about 27° C. to about 28° C. and the cells are kept suspended by means of an impeller rotating at about 200 rpm.

During operation, the replenishment medium, housed in a 10 liter glass vessel, is pumped to fluid inlet 303 of the extra-lumenal partition 320 of the hollow fiber dialysis device by means of a suitable pump, such as a Masterflex L/S Model 7520-00 with dual Easy-Load II Model 77200-62 pump heads with flexible silicone tubing, 6.4 mm i.d. size (Masterflex, size 15).

Medium progresses through the extralumenal chamber, finally exiting the hollow fiber filter device 304 and returning to the medium replenishment vessel 210 through flexible silicone tubing. Tubing to tubing connections are Swagelok 8 mm port connectors. Glass to tubing connections are secured by cable ties. Replenishment medium can be selected from any number of suitable sources including but not limited to SF-900. An optimum rate of flow through the replenishment medium loop is about 100 ml/min but the process operates satisfactorily at speeds as low as about 10 ml/min, as high as about 3000 ml/min. Optimum flow rates can be related to hollow fiber membrane area.

An external vent tube 214 with a filter attached to maintain sterility can be regulated as required by means of a clamp or ball valve.

Simultaneously, medium with suspended cells are continuously pumped from the stirred tank bioreactor by means of pump such as a Masterflex L/S Model 7520-00 with dual Easy-Load II Model 77200-62 pump heads with 6.4 mm i.d. size flexible silicone tubing (Masterflex, size 15).

The optimum rate of flow through the loop is about 100 m/min but the process operates satisfactorily at speeds as low as about 13 ml/min although some cell lines begin to settle out in the loop at this speed and at flow rates as high as about 3000 ml/min. above which shear forces increase to the point of inducing measurable cell damage. This cell suspension is first passed through a Y or T valve 130 where viral innoculum can be added to the cell suspension. The cell suspension next passes to the lumen of the hollow fiber filter 310 by way of the lumen input manifold 301 (A/G Technology, Corp; model CFP-6-D-8A, 0.65 micron pore size, 0.41 m$^2$ membrane surface area) where exchange occurs between the nutrient-rich replenishment medium and the cell medium containing metabolic waste products. The hollow fiber with dialysis, ultrafiltration and microfiltration properties can range in pore size from 30 kD cutoff to 0.65 μM diameter. Filters of pore sizes smaller than 30 kD cutoff may not provide adequate diffusion while those larger than 0.65 μM diameter may allow cells to pass through to the medium replenishment loop, reducing the activity within the bioreactor (although these parameters can be varied by the skilled artisan depending on the particular cells used or depending on the size of the cells in the bioreactor system and process; e.g., depending upon physical characteristics of particular cells). The membrane surface area can range from 0.042 m$^2$ to 4.2 m$^2$ to provide adequate exchange of replenishment nutrients and metabolic waste products in a 1 L culture.

Nutrients pass along a concentration gradient from the replenishment medium side of the hollow fiber filter to the cell suspension side of the device. Metabolic waste products pass along a concentration gradient from the cell suspension side of the hollow fiber filter to the replenishment medium side of the device. The cell suspension is next passed through an oxygenation device 150, such as the OXY-1 hollow fiber oxygenator (UniSyn Technologies). Alternatively or additionally oxygen can also be directly sparged in-line. For instance, oxygenation loop 150 can be omitted or supplemented by oxygen directly sparged into the system via line 130a (a selenoid such as selenoid 156 can be added to line 130a). "In-line sparging" can mean adding oxygen directly into the circulating cell culture, advantageously upstream or prior to return of the circulating cell culture to the bioreactor; and, preferably the oxygen is directly added to the circulating cells prior to or upstream of any dialysis means. This is in contrast to adding oxygen into the bioreactor. In other embodiments oxygen can be supplemented through the medium recirculation loop or through the hollow fiber filter unit. In any of these cases oxygen is advantageously maintained at about 60% of saturation relative to air (with constant variation permissible as herein discussed). An oxygen probe 114a can be connected to a control unit (microprocessor, processor, computer) which can regulate the flow of oxygen through selenoid 156 into input 154. Thus, a simple embodiment can involve an apparatus as illustrated in FIGS. 1-4 and 9, wherein sensors/probes 114 is includes sensor/probe 114a connected to a control unit that regulates the flow of oxygen through input 154 such that the oxygen is advantageously maintained at a substantially constant saturation or concentration (e.g., sensors/probes/control for pH, carbon dioxide can be omitted; sensor/probe/control for temperature may be present or omitted, for instance if system run at room temperature advantageously in room that is kept at fairly constant temperature).

Depending on the oxygenation site, pressure equalization between the bioreactor and the medium vessel may be required i.e. a line connecting both vessels' vent ports can be incorporated.

Cells can be returned to the bioreactor in a medium high in oxygen content and nutrients.

The replenishment nutrient stream returns to the replenishment nutrient vessel with added metabolic waste products and reduced in nutrients. Through the use of valves in the medium recirculation loop, the replenishment medium vessel can be refilled as needed, either because of nutrient depletion or waste product accumulation. Or the entire medium vessel can be replaced with similar of different medium, such as switching between a growth optimized medium and an expression optimized medium.

As mentioned herein, these activities can be automated, e.g., through the use of a computer, microprocessor or processor. For instance, as discussed, valves 231 and 232 and 233 can be automated, with valves 231 and 232 opening at predetermined times for sampling through line 230c, and based upon the data, additional medium added, and/or the medium replaced, and/or the medium further in line filtered or dialyzed. And, as discussed, further in line filtering or dialysis and adding of medium can be part of an automated process, e.g., employing valve 240.

The replacement of media too can be automated; for instance, "old" media can be removed via valve 232 (e.g., with a flow being from line 260a with valve 231 open for flow through both lines 260b and 230b or only through 230b or with flow being though line 260c through valve 231 to line 260b and valve 233 set for flow to continue to both lines 230a and 260a) while "fresh" or "new" or "different" media (as desired) added via valve 240 in a commensurate or sufficient amount relative to the removal at valve 232, over a period of time. Or, at lines 250 and 260 there can be T or Y valves that connect to a second media reservoir and when a particular period of time has passed or particular data is sensed e.g., at line 230c (such as glucose/nutrient and/or ammonia/waste concentration), these valves are engaged such that the system is in communication with the second media reservoir (either alone or in conjunction with the first media reservoir). Thus, media reservoirs (two or more media reservoirs) can be serially connected and activated for automatic changing of media.

Further, and additionally or alternatively, the replacement of media can be by means of a "tracer". More in particular, as "old" media can be removed via valve 232 (e.g., with a flow being from line 260a with valve 231 open for flow through both lines 260b and 230b or only through 230b or with flow being though line 260c through valve 231 to line 260b and valve 233 set for flow to continue to both lines 230a and 260a) with "fresh" or "new" or "different" media (as desired) added via valve 240, the media being added can contain a nutrient, electrolyte or some other chemical or physical moiety that is not deleterious to the system, and preferably advantageous to the system (such as a nutrient or electrolyte beneficial for the cells or a particular cell phase) that is not present in the "old" media being removed; a tracer.

For instance, the tracer can be a particular nutrient or electrolyte in the new media that is not in the old media It can function as a tracer because its concentration or how it affects a parameter, such as pH or conductivity, can be used as a measure for the endpoint of adding new media.

Consider, for example, that the tracer is a particular nutrient or electrolyte that can pass through the dialyzing means into the cell culture. As the concentration of that nutrient in the cell culture reaches a desired value and/or as the pH and/or conductivity of the cell culture changes to a desired value (e.g., as sensed at 114), such is indicative of the "old" media having been sufficiently replaced by the "new" media; e.g., microprocessor, processor or computer obtaining data from sensor 114 has a function F1 asking when concentration of tracer (e.g., nutrient and/or electrolyte) "[tracer]" in cell culture medium and/or cell culture medium pH and/or cell culture conductivity=value "C" (or C1 for tracer and/or C2 for pH and/or C3 for conductivity–e.g., representative of a desired amount of the nutrient or electrolyte in the cell culture from the new media), then cease adding new media and cease removing old media (stop adding via valve 240 and/or removal at valve 232); and, this function F1 can come into play after an earlier function began the process of adding new media and removing old media (that earlier function can be a function of a period of time having passed from the initiation of use of the old media in the media loop, or in response to other parameters such as levels of waste and/or nutrient in the cell culture, e.g., if waste higher than a desired level and/or nutrient lower than a desired level). (F1: C (and/or C1 and/or C2 and/or c3)=[tracer] and/or set pH and/or set conductivity– if yes, then close removal and/or addition valves; if no, continue with removal and/or addition.)

"Tracing" can also be performed exclusively in the media loop. For instance, a sensor at the removal valve, e.g., can detect the level of the tracer, and the computer, processor, microprocessor cease addition of new media and/or removal of old media based on the level of tracer detected at that point. In this way, the tracer can be a physical and/or inert entity and/or that which does not pass through or need to pass the dialysis filter.

Moreover, from the foregoing, the invention accordingly comprehends that there be at least one media reservoir, e.g., that there can be two or a plurality of media reservoirs. In similar fashion, bioreactors can be serially connected and automated, e.g., for automatically changing or increasing the cells in the system.

Additionally or alternatively, cell density or cell count can be measured at line 140a or 130a, and when a certain cell density is achieved, the microprocessor, processor, or computer can allow for introduction of a vector to infect or transfect the cells (e.g., through the other of lines 140a and 130a) and/or for changing of media and/or adding of ingredients (new ingredients or additional ingredients) to the media (via lines as discussed above, e.g., via line 240a and valve 240). For example, the computer, processor or microprocessor can take cell density/count measurement(s) via line 140a or 130a at certain times; if the measurement equals or exceeds a set value, then the vector is added (e.g., through the other of lines 140a and 130a), so that the cells can be infected and/or transfected, such as with a virus or vector, for instance, a recombinant vector or virus, e.g., a baculovirus. Accordingly, the system can allow for automatice infection/transfection at a point of optimal cell density/count. For example, at a cell density/count of about 4.5 million or higher, such as at about 5 million or about 10 million or about 15 million or about 16 million or about 19 million or about 22 million or higher (e.g., with insect cells; see, e.g., Examples, infra), the vector can be added. The skilled artisan, without undue experimentation, can set the optimal cell density/count level for infection/ transfection, from this disclosure and the knowledge in the art, considering such factors as the type of cell and the vector or virus being employed. On this point, it is noted that Wedgewood Technology Incorporated (San Carlos Calif.; www- .wedgewoodtech.com/web/index.htm) makes an absorbance probe (model BT65) that can be used for measuring cell density (as do other commercial suppliers). The Wedgewood Technology BT65 can be used with their model 612 single beam photometer or their model 653 absorbance monitor. The BT65sensor/653 monitor has analog outputs that can be connected to a computer, processor or microprocessor via an analog to digital interface (converter), without any undue experimentation. Thus, apparatus for measuring cell density are known in the art (e.g., absorbance sensors/monitors for measuring cell density) and can be used in conjunction with the invention (e.g., by connecting outputs from such units, for instance via an analog to digital converter or interface to a computer, processor or microprocessor), without any undue experimentation. Moreover, the invention comprehends that infection/transfection of cells can be automated, as can the replacement or supplementing of media; for instance, on the basis of cell density/count measurement.

Further, it is noted that the valves 140, 130, 240 and the loop 230 (via lines 140a, 130a, 240a and 230c, respectively) can be employed for removing expressed products from the system; e.g., removal of fluid from one port and replenishment or addition back into system when protein removed or with fresh or new fluid added to make up for that removed for product removal via another port. For instance, a suitable port can be connected to a separation means, e.g., a dialysis means or other means that may remove the expressed product without disrupting the cells if they are present in the fluid and the fluid thereafter returned to the system (with or without addition of new or fresh fluid); or a suitable port can be connected to means for processing the cell culture for expressed product isolation (e.g., means for cell lysis or otherwise extracting protein from the cell) and means for purifying and/or isolating the expressed product, with replacement added to the system via another port.

In addition, apparatus and methods of the invention can be used with other means for increasing cell growth and/or recombinant product expression, e.g., nutrient media, nutrients, etc. that enhance cell growth; promoters such as strong promoters or multiple copies of inserted exogenous coding nucleic acid (e.g., DNA) that can lead to enhanced expression levels.

A better understanding of the present invention and of its many advantages will be had from the following non-limiting Examples, given as a further description of the invention and as illustration of it.

EXAMPLES

Example 1

Growth of *Spodoptera frugiperda* (Sf900+) Cells in High-Density Dialysis Bioreactor with In-Line Oxygen Sparging Two liters of *S. frugiperda* Sf900+ (also called Sf900 in text) insect cells were seeded at $1.5 \times 10^6$ cells/mL (see FIG. 5). Oxygen was supplied initially by direct sparging at 60 L/hr and maintained at 60% saturation relative to air with an oxygen probe in the bioreactor connected to a solenoid regulating the flow of oxygen. The temperature of the cells was maintained at 28° C. and the cells were kept in suspension with an impeller rotating at 200 rpm. The pH of the media is generally 6.2. The cells doubled approximately every 24 hours and were $8.2 \times 10^6$ cells/mL by day 3. On day 3 the cells from the bioreactor were circulated at 100 m/min through silicon tubing connected to the lumen of a hollow fiber filter (A/G Technology, Corp; model CFP-6-D-8A, 0.65 micron pore size, 0.41 m² membrane surface area) then back to the bioreactor with a peristaltic pump (Masterflex L/S Model 7520-00 with dual Easy-Load II Model 77200-62 pump heads. Using the hollow fiber filter the cells concentrated to 1 liter to a density of $16.6 \times 10^6$ cells/ml. An external vessel with 9 L of media was connected to the second pump head on the same peristaltic pump and media was circulated through silicon tubing at 100 ml/min from the vessel, through the external compartment of the hollow fiber filter, and back to the media vessel. Effective pore size of a hollow fiber filter ranges from a lower limit of 0.05 μM to an upper limit of 0.65 μM (30,000 d mol. Wt.) which allows for diffusion across the membrane without leakage of cells across the filter. Effective flow rates through a hollow fiber filter range from 10 mL/min to 3000 mL/min. Below 10 mL/min cells settle out of suspension and above 3000 mL/min shear forces begin to disrupt cells. At 4 days the cells were at $26 \times 10^6$ cell/mL and the oxygen rate was increased to 90 L/hr in order to maintain the dissolved oxygen at 60% saturation (relative to air). At 5.1 days the cell density was $45.9 \times 10^6$ cells/mL and sparging oxygen directly into the bioreactor was no longer sufficient to keep the dissolved oxygen in the cells at 60%. Direct sparging was stopped and the oxygen line was connected directly to the circulating cells with a Y-connector at a position following the pump and before the hollow fiber filter. The oxygen flow rate was reduced from 90 L/hr to 9 L/hr. This so-called in-line sparging restored the dissolved oxygen level to 60% even with a 10-fold reduction in the oxygen flow rate. The reduced oxygen flow has the added advantages of reducing foaming and associated cell damage which is minimal in comparison to direct sparging with a high rate of oxygen flow.

Sf900+ cells doubled approximately every 24 hours with 97% or higher viability and grew to $74.6 \times 10^6$ cells/ml (FIG. 5). In a similar experiment where in-line sparging was used throughout the growth of Sf900+ cells in a 3 L bioreactor the cells reached the highest density every reported for insect cells of $93.4 \times 10^6$ cells/ml and a viability of 97.4%. Cell growth was examined numerically and closely fits an exponential growth curve of the form $y=ce^{bx}$ where y is the cell density, x is the time, c and b and constants, and e is the natural log. An exponential curve is show in FIG. 5 that closely fits (R-squared statistic equals 0.9189) the growth of the Sf900+ cells in the dialysis bioreactor.

Example 2

Yields of AcNPV Polyhedrin Protein in Standard and High-Density Cultures

One liter of Sf900+ cells were infected with AcNPV baculovirus using an MOI of 0.5 pfu/cell at the standard density of $1.5 \times 10^6$ cells/mL or at $16.0 \times 10^6$ cell/mL. The high-density culture was maintained in a 3-Liter dialysis bioreactor (Applicon) as described in Example 1 with continuous in-line sparging of oxygen at a flow rate of 9 L/hr. The oxygen was maintained in the high-density bioreactor throughout infection at the set point of 60% saturation of air. After 4 days the infected cells were collected and cellular proteins analyzed on SDS-polyacrylamide gels. The levels of polyhedrin protein were measured (FIG. 6) using a standard protein assay (BCA, Pierce). At $1.5 \times 10^6$ cells/ml, 800 milligrams of polyhedrin protein were produced per liter of infected cells. In the high-density culture over 10,374 mg produced per liter of polyhedrin was from 100 g of wet cells (biomass). This is the highest yield of polyhedrin protein ever reported for production in cultured insect cells. The relative yields of polyhedrin protein per gram of cells was over 100 milligrams/gram, higher than the 62.5 milligrams/gram of infected cells produced at the standard density demonstrating that the yield per cell of polyhedrin is actually higher in the high density cultures compared to standard conditions.

Example 3

Yields of Recombinant Hemagglutinin from Three Strains of Viral Influenza in Standard and High Density Cultures Sf900+ cells were infected at an MOI of 0.5 with AcNPV baculovirus expression vectors for A/Texas/36/91, A/Johannesburg/33/94, or A/Nanchang/933/95 viral influenza hemagglutinin at the standard density of $1.5 \times 10^6$ cells/mL or at $16.0 \times 10^6$ cell/mL in a high-density dialysis 3-liter bioreactor as described above in Example 1 and FIG. 1. At 3 days post infection the cells were collected and the proteins analyzed on SDS-polyacrylamide gels. Yields of total recombinant hemagglutinin proteins were determined using a scanning laser densitometry analysis (LKB Instruments) of the stained gels in comparison to known quantities of highly purified A/Texas/36/91, A/Johannesburg/33/94, or A/Nanchang/933/95 recombinant hemagglutinins. The yields of total recombinant hemagglutinin from all three strains increased 9.3, 10.1, and 11.1 fold in the high density cultures (FIG. 7) with yields of 840 mg/L, 710 mg/L, and 780 mg/L respectively. Although less than the levels observed at high cell density for polyhedrin, these yields of recombinant glycoprotein per liter are among the highest ever reported for any expression system. The yields of rHA per gram of wet cells (biomass) was as high or higher in the high density cultures compared to the relative yields in standard cultures.

Example 4

Production of Recombinant Baculovirus in High Density Cultures

The inventive high density bioreactor system and process can also be used to produce viruses, for instance, recombinant baculoviruses in Sf900+ cells. Table 1 are two examples of the production of infectious recombinant baculoviruses in Sf900+ cells infected at a density of about $15 \times 10^6$ cells/mL using the inventive bioreactor system and process as discussed in Example 1 and FIG. 1.

TABLE 1

Production of Recombinant Baculoviruses

| Cell line | Recombinant Baculovirus | MOI | Cell Density | Titer PFU/mL |
|---|---|---|---|---|
| Sf900+ | C6274 | 0.5 | $15.4 \times 10^6$ | $2.4 \times 10^8$ |
| Sf900+ | B6989 | 0.5 | $15.0 \times 10^6$ | $8.2 \times 10^8$ |

Example 5

Lack of Cell Aggregation with Sf900+ Cells in High Density Cultures

The degree of aggregation of Sf900+ cells was measured at a low ($1.38 \times 10^6$ cells/ml) and in two high-density cultures grown as described in Example 1 ($74.6 \times 10^6$ and $93.4 \times 10^6$ cells/ml). Sf900+ cells were counted using standard procedures in a hemocytometer. The number of aggregates with 5 or more cells in a clump and the number of viable and dead cells were recorded. The cell viability was >98% in both the low and high-density cultures. Less than 1.5% of the cells were aggregated in the low and both of the high density cultures, demonstrating the surprising result that Sf900+ cells grow in serum-free medium in the high-density dialysis bioreactors were essentially as a single-cell suspension of cells. The fact that Sf900+ cells do not aggregate avoids the problem associated with adding reagents or chemicals to the culture to prevent aggregation. Any aggregation would severely reduce the productivity of the cells due to diffusional barriers for nutrients or by-products or due to reducing their accessibility to virus infection.

Example 6

Long Term Sustainability of Exponential Growth

Figure 8:
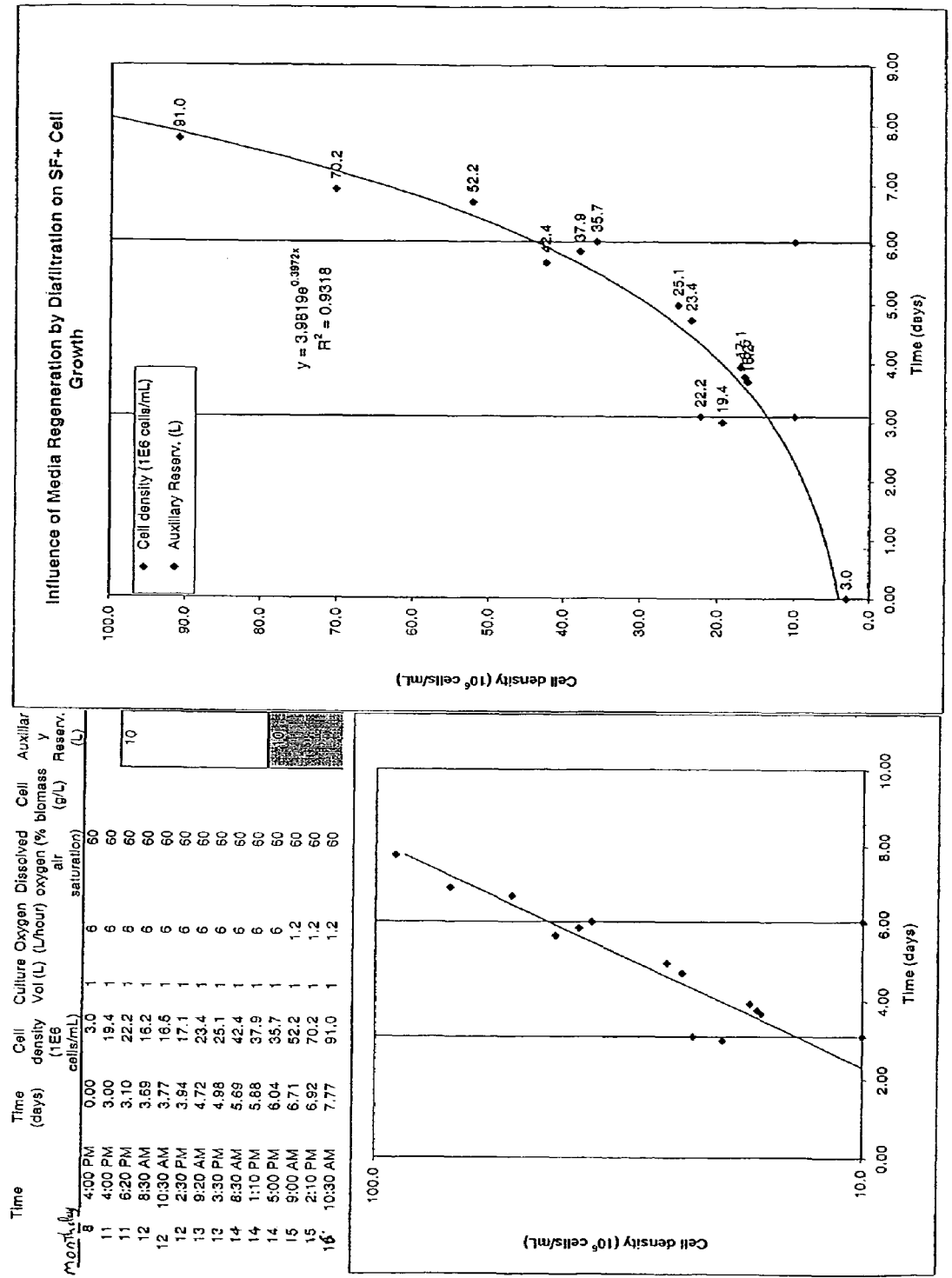
FIG. 8 shows a graph comparing the effects of oxygenation on growth.

One liter of S. frugiperda Sf900+ insect cells were seeded at $3.0 \times 10^6$ cells/mL as described in FIG. 8 in a system as described in Example 1 and FIG. 1 ("month day" in FIG. 8 means for instance the numerical day of a month, such that if the month were January, the "month days" in FIG. 8 illustrate readings on the $8^{th}$, $11^{th}$, $12^{th}$, $13^{th}$, $14^{th}$, $15^{th}$ and $16^{th}$ of January—the month—with time zero occurring on the $8^{th}$). Oxygen was supplied initially by direct sparging at 6 L/hr and maintained at 60% saturation relative to air with an oxygen probe in the bioreactor connected to a solenoid regulating the flow of oxygen. The temperature of the cells was maintained at 28° C. and the cells were kept in suspension with an impeller rotating at 200 rpm. The cells doubled approximately every 24 hours and were $19.4 \times 10^6$ cells/mL by day 3. On day 3 the cells from the bioreactor were circulated at 100 ml/min through silicon tubing connected to the lumen of a hollow fiber filter (A/G Technology, Corp; model CFP-6-D-8A, 0.65 micron pore size, 0.41 m² membrane surface area) then back to the bioreactor with a peristaltic pump (Masterflex L/S Model 7520-00 with dual Easy-Load II Model 77200-62 pump heads. An external vessel with 9 L of replenishment medium was connected to the second pump head on the same peristaltic pump and media was circulated through silicon tubing at 100 ml/min from the vessel, through the external compartment of the hollow fiber filter, and back to the media vessel. At 6 days the cells were at $35.7 \times 10^6$ cell/mL and the external vessel with 9 L of replenishment medium was replaced with a new vessel containing 9 L of fresh replenishment medium. At 6.7 days the cell density was $52.2 \times 10^6$ cells/mL and sparging oxygen directly into the bioreactor was no longer sufficient to keep the dissolved oxygen in the cells at 60%. Direct sparging was stopped and the oxygen line was connected directly to the circulating cell line with a Y-connector at a position subsequent to the pump but ahead of the hollow fiber filter. The oxygen flow rate was reduced from 6 L/hr to 1.2 L/hr. This so-called in-line sparging maintained the dissolved oxygen level at 60%.

Sf900+ cells doubled approximately every 24 hours with 97% or higher viability and grew to $91 \times 10^6$ cells/ml (FIG. 8), near to the record density reported in Example 1. Cell growth was examined numerically and closely fits an exponential growth curve of the form $y = ce^{bx}$ where y is the cell density, x is the time, c and b are constants, and e is the natural log. A plot of the data and the calculated exponential curve is show in FIG. 5 that closely fits (R-squared statistic equals 0.9318) the growth of the Sf900+ cells in the dialysis bioreactor.

Example 7

Inline Oxygenation

To determine the effect of in line sparging on expression in HD cultures two cultures were set up containing $22 \times 10^9$ cells which were infected with AcNPV baculovirus expression vector for A/Beijing/262/95 viral influenza neuramimidase (NA). The culture with standard sparging had oxygen supplied at 2 L/min through a single 5 mm tube immersed in the culture. The test culture was sparged at 0.2 L/min through the lumen side of the hollow fiber dialysis device. The cultures were harvested 72 hours post-infection (hpi) and samples were subjected to SDS-PAGE and western blot analysis. Other samples were assayed for NA activity.

A. Culture with Standard Sparging

A 2 L 72 hour old culture of SF+ cells in PSFM medium in a 3 L Applikon fermentor was equipped with the high density apparatus including a 0.16 m², 0.65 μm pore hollow fiber filter and a 5 L bottle of PSFM. Cells and medium were circulated through the filter at 100 mls/min using a double headed peristaltic pump. Temperature was maintained at 28° C. using a heat blanket, temperature probe and a Valley instruments controller. Dissolved oxygen was maintained at 60% of air using an Ingold DO probe and a Valley instruments controller. Oxygen was supplied through a single 5 mm tube positioned directly under the impeller. Agitation was done using a marine impeller spun at 200 rpm.

The cells in this culture grew to a density of $10.8 \times 10^6$ cells/ml ($21.6 \times 10^9$ total) in 24 hours. They were infected at an M.O.I. of 0.5 with NA innoculum. The culture was harvested 72 hpi at which time it contained $18.0 \times 10^9$ total cells of which 41% were viable. The culture was harvested by centrifugation at 3000×G for 1 hour. The filter was flushed with 1 L of the diafiltrate and the cells pelleted at 3000×G for 1 hour. Pellet biomass data is shown below

|  | Volume | Pellet |
|---|---|---|
| HD | 1650 ml | 77.2 g |
| Diaf wash | 1000 ml | 3.6 g |
| Total biomass |  | 80.8 g |

B. Standard Density Control Culture

A 500 ml culture of SF+ cells at $1.5 \times 10^6$ cells/ml was set up in a 3 L spinner flask and infected at an M.O.I. of 0.5 with NA innoculum. The culture was collected 72 hpi and the cells pelleted at 3000×G for 1 hour. The cell pellet from this culture weighed 4.0 g. Samples from this culture were subjected to SDS-PAGE and western blot analysis. They were also tested for NA activity.

C. Culture with In Line Sparging

A 2 L culture of SF+ cells in PSFM medium in an Applikon 3 L fermenter was configured for a HD culture similar to that for the standard sparging culture. The difference was that this culture was equipped for in line sparging. Instead of oxygen being delivered through a single tube a Y connector was inserted between the cell circulation pump head and the hollow fiber filter. Oxygen was added through the filter at 0.2 L/min while being monitored through the DO probe in the fermentor.

When the cells in this culture grew to a total of $21.9 \times 10^9$ cells (1.9 L at $11.5 \times 10^6$ cells/ml) they were infected with NA innoculum at an M.O.I. of 0.5. A 100 ml culture of SF+ cells at the standard density of $1.5 \times 10^5$ cells/ml in a 250 ml spinner was infected with NA innoculum at an M.O.I. of 0.5 to serve as a control.

Samples for gel analysis were taken at 24, 48 and 72 hpi. The culture was harvested 72 hpi. The cells were pelleted as above and weighed.

|  | Volume | Pellet |
|---|---|---|
| In line O$_2$ HD | 1900 mls | 110.4 g |
| Diaf wash | 850 mls | 10.2 g |
| Total biomass |  | 120.6 g |

Biomass Summary Table

Note: All biomass values are adjusted for 2 L of culture for comparison purposes.

| Culture type | Total Biomass (g) |
|---|---|
| Standard Culture | 20 |
| High Density Culture with standard sparging | 80.8 |
| High Density Culture with in-line sparging | 120.6 |

As the biomass data demonstrates, in this example, in-line sparging increased total cell biomass by approximately 50% even as oxygen was delivered at a rate tenfold lower than standard sparging.

Example 8

High Density Growth of CHO Mammalian Cells and Expression of Human M-CSF

Figure 11:
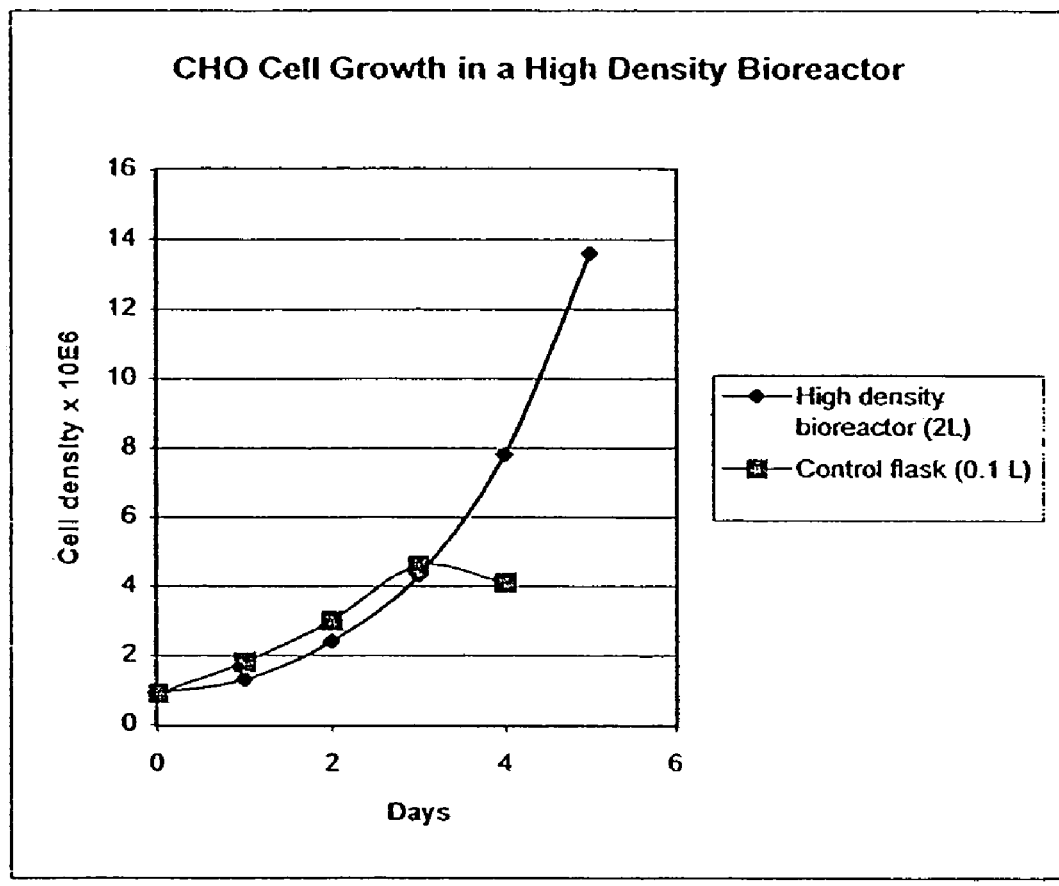

To measure the ability of the present invention to support the growth to high density of cells other than insect cells, such as mammalian cells, and to demonstrate that this can result in improved expression of recombinant protein, the following experiment was performed. A Chinese hamster cell line that had been engineered to express human macrophage colony stimulating factor (M-CSF CHO cells) were obtained from HyClone Laboratories Inc (Logan, Utah) (cf U.S. Pat. Nos. 5,650,297, 5,567,611, and 4,847,201, inter alia, regarding DNA encoding M-CSF and CHO cells expressing M-CSF). The cells were maintained using standard conditions in shaker flasks on a cell culture shaker (135 rpm) in a 37° C. incubator kept at 5% $CO_2$ and maintained in HyQ PF CHO medium (HyClone Laboratories). M-CSF CHO cells were seeded on day 0 at a density of $0.9 \times 10^6$ cells/ml in a volume of 1.5 liters in a Bioflo 3000 bioreactor (New Brunswick Scientific, Edison N.J.) and maintained at 37° C. with an agitation speed of 50 rpm, dissolved oxygen set at 50% relative to air, and pH set at 7.3. By day 1 the cells had grown to $1.3 \times 10^6$ cells/ml and the high-density apparatus of the invention (FIG. 1, Example 1) was assembled and the cells introduced therein and an experiment according to the invention performed. The culture medium from the bioreactor was circulated at 50 ml/min through the lumen of an 0.45 micron, 0.45 sq ft A&G hollow fiber filter. HyQ PF CHO medium was put into 5 L bottle (dialysis medium) and maintained at 37° C. and circulated at 50 ml/min through the hollow fiber filter. On day 3 the 5 L bottle of media was replaced with a 5 L bottle of fresh HyQ PF CHO medium and it was maintained at 37° C. and circulated at 50 ml/min through the hollow fiber filter. On days 2, 3, 4 and 5 the cells in the high-density bioreactor doubled about every 24 hours and by day 5 were at a density of $13.6 \times 10^6$ cells/ml (FIG. 11). In a control flask, 100 ml of M-CSF CHO cells were set up at $0.9 \times 10^6$ cells/ml and maintained under standard conditions for 4 days. The cells doubled approximately every 24 hours and reached a maximum of $4.6 \times 10^6$ cells/ml on day 3 (FIG. 11).

Therefore, the high-density bioreactor and methods of the invention produced at least about 4 times the number of cells per unit volume as under standard culturing conditions.

M-CSF CHO cells have been engineered to express the human gene produce for M-CSF. Samples of the culture media from day 0 and day 4 in the high-density bioreactor and in the control flask were obtained from the experiment described above and the levels of human M-CSF (Hu M-CSF) were measured using a commercial assay kit. The follow Table summarizes the levels of Hu M-CSF produced by the CHO cells and secreted into the culture media in the high density 2 L bioreactor at days 0 and 4, in the 5 L of dialysis media at days 3 and in the 5 L of the second bottle of dialysis media at day 4, and in the 100 ml control flask at days 0 and 4. The total production of Hu M-CSF produced in the control flask was at a level of 3.0 mg/L. Whereas in the high-density bioreactor, a total of over 11.68 mg/L of Hu M-CSF were produced which represents an increase of at least over 3.9 times the yield of Hu M-CSF as produced in M-CSF CHO cells maintained under standard conditions. In summary, a mammalian CHO cell line grew to at least about 4 times the cell density and produced at least about 3.9 times the levels of secreted Hu M-CSF.

Thus, the invention is applicable to various cell lines and can result in increased cell density and/or increased protein expression.

| Cell Culture | Source | Volume (ml) | Days | Cells/ml × 10E6 | Hu M-CSF mg/L culture |
|---|---|---|---|---|---|
| High density bioreactor (2L) | bioreactor | 2000 | 0 | 0.9 | 0.51 |
| | dialysis media | 5000 | 3 | 7.8 | 5.12 |
| | bioreactor | 2000 | 4 | 13.6 | >4.0* |
| | dialysis media | 5000 | 4 | 13.6 | 2.56 |
| | TOTAL Hu M-CSF | | | | >11.68 |
| Control flask (100 ml) | flask | | 0 | 1.3 | 0.38 |
| | flask | | 4 | 4.1 | 3.0 |
| | TOTAL Hu M-CSF | | | | 3.0 |

(*Expression was so high that it was greater than 4 and off the scale of the assay; it is expected that the increase is at least 4-fold and can be 10-fold or more.)

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. An apparatus for growing cells comprising:
   (a) at least one bioreactor for cell culture;
   (b) at least one vessel for culture medium;
   whereby the bioreactor and vessel are in fluid communication, and
   wherein the bioreactor and/or vessel are optionally stirred;
   (c) a dialysis means for circulating culture medium and/or cell culture,
   whereby there is a first, cell culture loop between the bioreactor and the dialysis means and a second, media replenishment loop between the vessel and the dialysis means;
   (d) in operation dialysis between the culture medium and the cell culture;
   (e) at least one means for delivery of oxygen comprising a hollow fiber filter oxygenator,
   whereby the oxygen is delivered directly to cells in a circulating loop of cells before cell entry into the hollow fiber filter.

2. The apparatus of claim 1 wherein the means for delivery of oxygen comprises at least one or more of the following:
   hollow fiber filter oxygenator;
   means for in-line sparging;
   means for delivery of at least one oxygen-containing compound that releases dissolved oxygen into cell culture;
   means for delivery of oxygen positioned upstream of input of circulating cell culture returning to the bioreactor;
   means for delivery of oxygen providing an average dissolved oxygen concentration of about 60%;
   means for delivery of oxygen provides an average dissolved oxygen concentration of greater than about 40%; and,
   means for delivery of oxygen provides an average dissolved oxygen concentration between about 30% and 90% or between about 40% and about 80% or between about 50% and 70%.

3. The apparatus of claim 1 wherein the dialysis means comprises at least one semi-permeable membrane and/or at least one means for delivery of oxygen into the cell culture loop.

4. The apparatus of claim 1 wherein the means for delivery of oxygen comprises at least one or more of the following:
   a hollow fiber filter oxygenator;
   means for in-line sparging;
   means for delivery of at least one oxygen-containing compound that releases dissolved oxygen into cell culture; and,
   means for delivery of oxygen positioned upstream of input of circulating cell culture returning to the bioreactor.

5. The apparatus of claim 1 further comprising one or more of the following:
   means for measuring physical and/or chemical parameter(s) of the cell culture and/or the culture medium;
   means for measuring dissolved oxygen concentration;
   means for measuring pH;
   means for measuring temperature;
   means for measuring pH and means for measuring dissolved oxygen;
   means for measuring cell density or amount of cells;
   means for adjusting physical and/or chemical parameter(s) of the cell culture and/or the culture medium in response to data from the measuring means;
   means to adjust temperature;
   means for adjusting pH;
   means for adjusting dissolved oxygen concentration
   means for adjusting dissolved carbon dioxide concentration;
   means for adjusting physical and/or chemical parameter(s) of the cell culture and/or the culture medium in response to data from the measuring means;
   means to adjust temperature;
   means for adjusting pH;
   means for adjusting dissolved oxygen concentration;
   means for adjusting dissolved carbon dioxide concentration;
   means for adding a vector in response to a cell density or cell amount measurement;
   means for adjusting dissolved oxygen and means for adjusting dissolved carbon dioxide, whereby in response to pH measurement(s), dissolved carbon dioxide levels are adjusted.

6. The apparatus of claim 5 wherein:
   in response to dissolved oxygen measurement(s), dissolved oxygen levels are adjusted; and/or
   wherein pH is set to a desired level and carbon dioxide is adjusted when pH varies from the desired level, whereby the dissolved oxygen measurement varies periodically as a function of time; and/or,
   wherein the dissolved oxygen measurement varies from 30% to 90% or from 40% to 80% or from 50% to 70%; or, the dissolved oxygen measurement averages about 60%; and/or,
   wherein the dissolved oxygen measurement varies from high value to low value over about 10 to about 30 minutes or over about 20 minutes; and/or,
   wherein a plot of the dissolved oxygen measurement as a function of time comprises a sin wave.

* * * * *

UNITED STATES PATENT AND TRADEMARK OFFICE
CERTIFICATE OF CORRECTION

PATENT NO. : 7,598,075 B2
APPLICATION NO. : 11/097994
DATED : October 6, 2009
INVENTOR(S) : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 454 days.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,598,075 B2 | Page 1 of 1 |
| APPLICATION NO. | : 11/097994 | |
| DATED | : October 6, 2009 | |
| INVENTOR(S) | : Gale E. Smith et al. | |

It is certified that error appears in the above-identified patent and that said Letters Patent is hereby corrected as shown below:

ON THE COVER OF THE PATENT insert

--Related U.S. Application Data

(62)  Divisional of application No. 09/484,886, filed on 01/18/2000, pending

(60)  Provisional application No. 60/118,816, filed on 02/05/1999 and provisional application No. 60/162,354, filed on 10/29/1999--

Signed and Sealed this

Twenty-second Day of February, 2011

David J. Kappos
*Director of the United States Patent and Trademark Office*